US009340878B2

(12) United States Patent
Arno et al.

(10) Patent No.: US 9,340,878 B2
(45) Date of Patent: May 17, 2016

(54) TPIR APPARATUS FOR MONITORING TUNGSTEN HEXAFLUORIDE PROCESSING TO DETECT GAS PHASE NUCLEATION, AND METHOD AND SYSTEM UTILIZING SAME

(75) Inventors: Jose I. Arno, Brookfield, CT (US); Joseph R. Despres, Middletown, CT (US); Shkelqim Letaj, Wolcott, CT (US); Steven M. Lurcott, Sherman, CT (US); Thomas H. Baum, New Fairfield, CT (US); Peng Zou, Ridgefield, CT (US)

(73) Assignee: ENTEGRIS, INC., Billerica, MA (US)

( * ) Notice: Subject to any disclaimer, the term of this patent is extended or adjusted under 35 U.S.C. 154(b) by 1024 days.

(21) Appl. No.: 13/375,053

(22) PCT Filed: May 28, 2010

(86) PCT No.: PCT/US2010/036747
§ 371 (c)(1),
(2), (4) Date: Jan. 21, 2012

(87) PCT Pub. No.: WO2010/138930
PCT Pub. Date: Dec. 2, 2010

(65) Prior Publication Data
US 2012/0114836 A1 May 10, 2012

Related U.S. Application Data

(60) Provisional application No. 61/182,527, filed on May 29, 2009.

(51) Int. Cl.
*G01N 31/00* (2006.01)
*C23C 16/52* (2006.01)
(Continued)

(52) U.S. Cl.
CPC .............. *C23C 16/52* (2013.01); *C23C 16/14* (2013.01); *G01N 21/3504* (2013.01)

(58) Field of Classification Search
CPC .......................... G01N 21/3504; G01J 5/0014
USPC ...................... 427/8; 702/24, 28, 30
See application file for complete search history.

(56) References Cited

U.S. PATENT DOCUMENTS

| 4,647,777 A | 3/1987 | Meyer |
| 4,816,294 A | 3/1989 | Tsuo et al. |

(Continued)

OTHER PUBLICATIONS

Adrian, P., "Sensor industry developments and trends", "Sensor Business Digest", Oct. 2001, Publisher: Vital Information Publication, Inc.

(Continued)

*Primary Examiner* — Michael Wieczorek
(74) *Attorney, Agent, or Firm* — Hultquist, PLLC; Steven J. Hultquist

(57) ABSTRACT

Apparatus and method for monitoring a vapor deposition installation in which a gas mixture can undergo gas phase nucleation (GPN) and/or chemically attack the product device, under process conditions supportive of such behavior. The apparatus includes a radiation source arranged to transmit source radiation through a sample of the gas mixture, and a thermopile detector assembly arranged to receive output radiation resulting from interaction of the source radiation with the gas mixture sample, and to responsively generate an output indicative of onset of the gas phase nucleation and/or chemical attack when such onset occurs. Such monitoring apparatus and methodology is useful in tungsten CVD processing to achieve high rate tungsten film growth without GPN or chemical attack.

9 Claims, 22 Drawing Sheets

(51) Int. Cl.
*G01N 21/3504* (2014.01)
*C23C 16/14* (2006.01)

(56) References Cited

U.S. PATENT DOCUMENTS

| | | | |
|---|---|---|---|
| 4,935,345 A | 6/1990 | Guilbeau et al. | |
| 5,047,352 A | 9/1991 | Stetter et al. | |
| 5,282,473 A | 2/1994 | Braig et al. | |
| 5,357,113 A | 10/1994 | Liston et al. | |
| 5,367,167 A | 11/1994 | Keenan | |
| 5,404,125 A | 4/1995 | Mori et al. | |
| 5,464,983 A | 11/1995 | Wang | |
| 5,589,689 A | 12/1996 | Koskinen | |
| 5,594,248 A | 1/1997 | Tanaka | |
| 5,650,624 A | 7/1997 | Wong | |
| 5,721,430 A | 2/1998 | Wong | |
| 5,782,974 A | 7/1998 | Sorensen et al. | |
| 5,834,777 A | 11/1998 | Wong | |
| 5,962,854 A | 10/1999 | Endo | |
| 5,963,336 A * | 10/1999 | McAndrew et al. | 356/437 |
| 5,967,992 A | 10/1999 | Canfield | |
| 6,045,257 A | 4/2000 | Pompei et al. | |
| 6,086,654 A | 7/2000 | Mulvaney, III et al. | |
| 6,122,042 A | 9/2000 | Wunderman et al. | |
| 6,348,650 B1 | 2/2002 | Endo et al. | |
| 6,370,950 B1 | 4/2002 | Lammerink | |
| 6,444,474 B1 | 9/2002 | Thomas et al. | |
| 6,469,303 B1 | 10/2002 | Sun et al. | |
| 6,617,175 B1 | 9/2003 | Arno | |
| 6,649,994 B2 | 11/2003 | Parsons | |
| 6,694,800 B2 | 2/2004 | Weckstrom et al. | |
| 6,762,410 B1 | 7/2004 | Wiechers et al. | |
| 6,821,795 B2 | 11/2004 | Arno | |
| 6,828,172 B2 | 12/2004 | Chavan et al. | |
| 6,875,399 B2 | 4/2005 | McVey | |
| 6,909,093 B2 | 6/2005 | Sato et al. | |
| 7,009,267 B2 | 3/2006 | Honboh | |
| 7,011,614 B2 | 3/2006 | Arno | |
| 7,033,542 B2 | 4/2006 | Archibald et al. | |
| 7,058,519 B2 | 6/2006 | Arno | |
| 7,129,519 B2 | 10/2006 | Arno | |
| 7,172,918 B2 * | 2/2007 | Arno | 438/50 |
| 7,351,976 B2 | 4/2008 | Arno | |
| 7,723,685 B2 | 5/2010 | Arno | |
| 2002/0049389 A1 | 4/2002 | Abreu | |
| 2002/0051132 A1 | 5/2002 | Ohno et al. | |
| 2004/0038442 A1 | 2/2004 | Kinsman | |
| 2004/0069942 A1 | 4/2004 | Fujisawa et al. | |
| 2005/0211555 A1 | 9/2005 | Archibald | |
| 2006/0219923 A1 | 10/2006 | Uchida et al. | |
| 2008/0006775 A1 * | 1/2008 | Arno et al. | 250/338.5 |

OTHER PUBLICATIONS

"IEEE 100 the Authoritative Dictionary of IEEE Standard Terms, Seventh Edition", Dec. 2000, p. 1174, Publisher: The Institute of Electrical and Electronics Engineering, Inc.

Mohn, J., et al., "Process Gas Analysis by FTIR for the Semiconductor Industry", "CTI Micro and Nano Technologies, Neuchatel", 2004, p. 1, Publisher: EMPA Technologies.

Schilz, J., "Applications of thermoelectric infrared sensors (thermopiles): Gas detection by infrared absorption; NDIR", "Thermophysica Minima", Aug. 22, 2000, pp. 1-11, Publisher: PerkinElmer.

Thermometrics Global Business, "Application note of thermopile IR sensors (Rev.02)", 2000, pp. 1-9.

Wilks, P., "The birth of infrared filtometry", "Spectroscopy Showcase", Mar. 2002, p. 14.

* cited by examiner

Pedestal 1

Pedestal 1

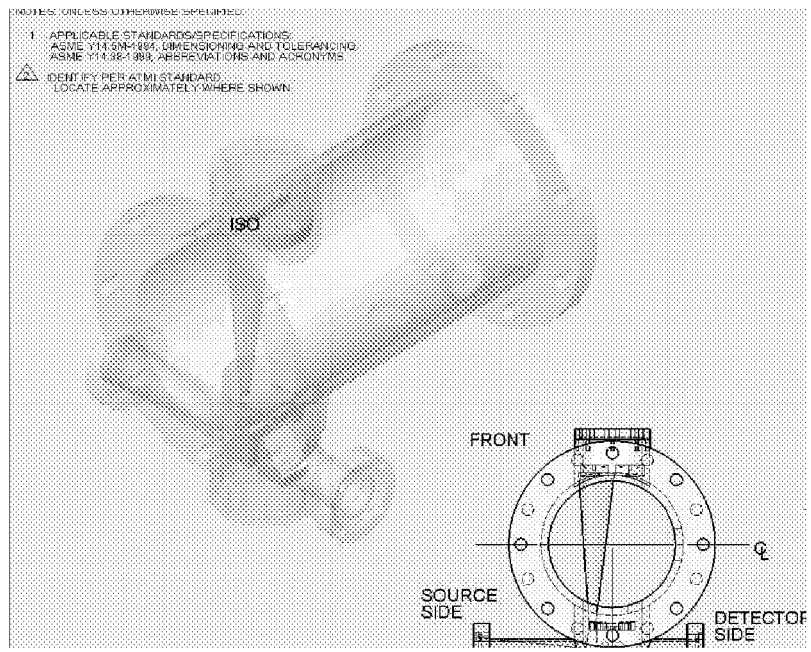
FIG. 10     FIG. 11
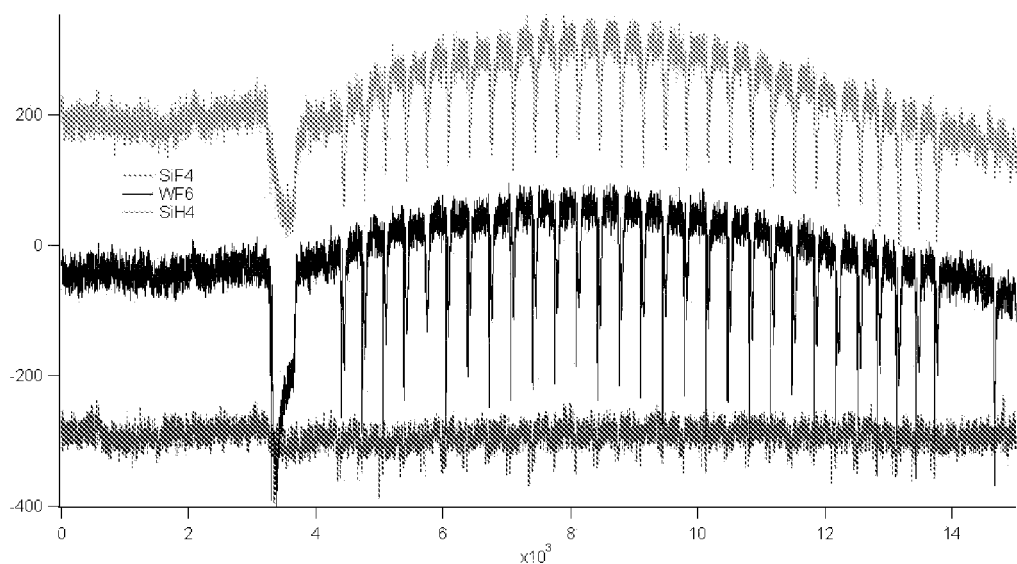
FIG. 12

$I_{SiF4} - I_{WF6}$

TPIR APPARATUS FOR MONITORING TUNGSTEN HEXAFLUORIDE PROCESSING TO DETECT GAS PHASE NUCLEATION, AND METHOD AND SYSTEM UTILIZING SAME

CROSS-REFERENCE TO RELATED APPLICATIONS

This application is a U.S. national phase under the provisions of 35 U.S.C. §371 of International Patent Application No. PCT/US10/36747 filed May 28, 2010, which in turn claims the benefit of priority under 35 USC 119 of U.S. Provisional Patent Application 61/182,527 filed May 29, 2009 in the names of Jose I. Arno, et al. for "TPIR APPARATUS FOR MONITORING TUNGSTEN HEXAFLUORIDE PROCESSING TO DETECT GAS PHASE NUCLEATION, AND METHOD AND SYSTEM UTILIZING SAME". The disclosures of such international patent application and U.S. provisional patent application are hereby incorporated herein by reference in their respective entireties, for all purposes.

FIELD OF THE INVENTION

The present invention relates to monitoring of processes by thermopile infrared (TPIR) detectors, and more specifically to a TPIR system arranged to monitor vapor deposition process installations that are susceptible to undesirable behavior of vapor deposition precursor species as a result of variable conditions in process equipment in such installation, e.g., occurrence of gas phase nucleation and chemical attack of surfaces or components. The invention in one aspect relates to chemical vapor deposition (CVD) of tungsten, and control of gas mixtures to suppress gas phase nucleation (GPN) of particulates and attack of titanium and silicon surfaces while effecting high rate tungsten deposition.

DESCRIPTION OF THE RELATED ART

In the manufacture of microelectronic devices, deposition of tungsten films by chemical vapor deposition is commonly practiced, using tungsten hexafluoride as a tungsten precursor and reducing gases such as hydrogen or silane.

The use of hydrogen in such application produces films with undesirable surface roughness, and induces occurrence of damaging reactions at exposed silicon and titanium surfaces, resulting in excessive leakage current and contact resistance, as well as decreased film adhesion of the tungsten film. For such reasons, silane is used to achieve high tungsten deposition rates and to reduce the incidence of silicon and titanium attack by tungsten hexafluoride or HF formed as a result of hydrogen reduction of tungsten hexafluoride.

Silane reduction of $WF_6$ to elemental tungsten, however, can take place in the gas phase, by the reaction $WF_6 + SiH_4 \rightarrow W(WSi) + SiF_4 + H_2 + HF$. Such gas phase nucleation of tungsten particles can result in significant incorporation of tungsten particles in the deposited film, and is desirably avoided.

Even when silane is used as a $WF_6$ reducing agent, however, chemical attack can be significant, depending on specific process conditions. In general, chemical attack and gas phase nucleation phenomena are interrelated, in that process conditions that suppress one of such phenomena tend to enhance the other.

Adhesion issues of tungsten films can be ameliorated by use of titanium/titanium nitride layers (referred to as a Ti:TiN liner), but if hydrogen is used as a reducing agent, the rate of tungsten film growth may be significantly reduced. Such reduced growth rate in turn necessitates longer periods for achieving films of the desired thickness, but such increased deposition periods allows any weaknesses or discontinuities in the Ti:TiN liner to facilitate chemical attack on the underlying material, and the $WF_6$ can attack the Ti:TiN liner to form $TiF_x$ species as defects in the product tungsten film, e.g., by the reaction $WF6 + TiN \rightarrow TiF4 + W + HF$.

In consequence of the foregoing issues, the art continues to seek improvements in tungsten deposition processes in microelectronic device manufacturing applications.

SUMMARY

The present invention relates to apparatus and process for monitoring vapor deposition installations wherein gas phase mixtures containing deposition species can cause gas phase nucleation and chemical attack depending on process conditions.

In one aspect, the invention relates to an apparatus for monitoring a vapor deposition installation wherein a gas mixture comprising gas species can cause gas phase nucleation and/or chemical attack under process conditions supportive of such behavior, the apparatus comprising: a radiation source arranged to transmit source radiation through a sample of said gas mixture; and a thermopile detector assembly arranged to receive output radiation resulting from interaction of the source radiation with the gas mixture sample, and to responsively generate an output indicative of onset of said gas phase nucleation and/or chemical attack when said onset occurs.

Another aspect of the invention relates to a method of carrying out vapor deposition, comprising contacting a substrate with a gas mixture containing gas species that can cause gas phase nucleation and/or chemical attack under process conditions supportive of such behavior, said process comprising:

impinging radiation on a sample of said gas mixture for interaction of the radiation with one or more gas species in the gas mixture to produce output radiation from said interaction having a characteristic that is indicative of onset of said gas phase nucleation and/or chemical attack when said onset occurs; and processing said output radiation to responsively generate an output indicative of onset of said gas phase nucleation and/or chemical attack when said onset occurs.

In a further aspect, the invention relates to a method of carrying out tungsten chemical vapor deposition to avoid incidence of gas phase nucleation and chemical attack in said deposition, wherein said chemical vapor deposition comprises contacting a gas mixture comprising $WF_6$ and $SiH_4$, with a Ti:TiN layer on a microelectronic device substrate, said method comprising monitoring at least one of $WF_6$, $SiF_4$ and $SiH_4$ in an effluent from the chemical vapor deposition by TPIR monitoring to detect onset of gas phase nucleation and/or chemical attack, and responsively controlling the chemical vapor deposition to avoid incidence or continuation of gas phase nucleation and/or chemical attack.

In yet another aspect, the invention relates to an apparatus for determining occurrence of gas phase nucleation in a chemical vapor deposition chamber having one or more windows, comprising an infrared radiation diode laser arranged to transmit IR radiation through a window into the chamber for interaction with vapor therein during chemical vapor deposition in the chamber to generate output radiation from such interaction, and a photodiode detector arranged to detect said output radiation transmitted through a same or different window of the chamber and to responsively generate an output indicative of occurrence or non-occurrence of gas phase nucleation in the chemical vapor deposition chamber.

A still further aspect of the invention relates to a method of determining occurrence of gas phase nucleation in a chemical vapor deposition chamber having one or more windows, comprising energizing an infrared radiation diode laser to transmit IR radiation through a window into the chamber for interaction with vapor therein during chemical vapor deposition in the chamber and generate output radiation from such interaction, detecting with a photodiode detector the output radiation transmitted through a same or different window of the chamber, and responsively generating an output indicative of occurrence or non-occurrence of gas phase nucleation in the chemical vapor deposition chamber.

Yet another aspect of the invention relates to a process for controllably maintaining a process within a predetermined operating regime, using a TPIR monitoring and control system including a monitoring cell adapted to receive material from the process, wherein the material in the monitoring cell interacts with infrared radiation generated by the monitoring system and infrared radiation resulting from such interaction is detected by a TPIR detector of the TPIR monitoring and control system as a TPIR monitoring output from the monitoring cell, said process comprising:

generating a TPIR monitoring output from the monitoring cell;
removing ambient radio frequency noise spikes from TPIR monitoring output to produce a first refined data output;
smoothing the first refined data output using a binomial smoothing algorithm to produce a second refined data output;
calculating slope and offset values for signals of material components monitored in the monitoring cell;
utilizing the slopes and offsets for the monitored material components to temperature correct the second refined output and produce a third refined output;
conducting a peak search algorithm of the third refined output and calculating peak heights of the monitored material components, to generate peak heights of such monitored material components, and determining from peak height differences of such monitored material components whether processing associated with the monitoring is within a predetermined operating regime; and
correspondingly modulating the process by adjustment of one or more operating parameters thereof, to maintain the process within the predetermined operating regime.

Another aspect of the invention relates to a TPIR monitoring and control system, comprising:
a monitoring cell adapted to receive material for monitoring;
an infrared source arranged to emit radiation that interacts with material in the monitoring cell to produce output infrared radiation resulting from such interaction;
a TPIR detector arranged to detect the output infrared radiation and responsively generate a TPIR monitoring output for material monitored in the monitoring cell;
a computational module arranged for:
  generating a TPIR monitoring output from the monitoring cell;
  removing ambient radio frequency noise spikes from TPIR monitoring output to produce a first refined data output;
  smoothing the first refined data output using a binomial smoothing algorithm to produce a second refined data output;
  calculating slope and offset values for signals of material components monitored in the monitoring cell;
  utilizing the slopes and offsets for the monitored material components to temperature correct the second refined output and produce a third refined output;
  conducting a peak search algorithm of the third refined output and calculating peak heights of the monitored material components, to generate peak heights of such monitored material components, and determining from peak height differences of such monitored material components whether processing associated with the monitoring is within a predetermined operating regime; and
a controller coupled with the computational module for correspondingly modulating the process by adjustment of one or more operating parameters thereof, to maintain the process within a predetermined operating regime.

Other aspects, features and embodiments of the invention will be more fully apparent from the ensuing disclosure and appended claims.

BRIEF DESCRIPTION OF THE DRAWINGS

FIG. 10 is a perspective view, and FIG. 11 is a front elevation view, of an in-line multi-pass cell arrangement wherein the monitoring apparatus optics are not exposed directly to the gas flow.

FIG. 12 is a graph of wafer processing data for a TPIR monitoring apparatus of the invention, for a 20 wafer lot, including the top $SiF_4$ spectrum, the intermediate $WF_6$ spectrum and the bottom $SiH_4$ spectrum, showing the differentiated character of the three spectra.

DETAILED DESCRIPTION

The present invention relates to apparatus and process for monitoring vapor deposition installations wherein gas phase mixtures containing deposition species can cause gas phase nucleation and chemical attack depending on process conditions.

The invention has particular utility for monitoring tungsten deposition systems where tungsten hexafluoride and silane are used as reagents for the deposition of tungsten on a substrate including a Ti:TiN liner. Although the invention is described hereinafter with particular reference to monitoring of tungsten CVD systems, it will be appreciated that the utility of the invention is not thus limited and that the invention may be usefully employed in a wide variety of process systems susceptible to chemical attack of substrates and gas phase nucleation as undesirable events in system operation.

With reference to the thermopile infrared detectors utilized in the apparatus of processes of the invention, TPIR assemblies of widely variant type may be usefully employed in the broad practice of the invention, including the TPIR assemblies and methodologies described in U.S. Pat. No. 6,617,175 issued Sep. 9, 2003, U.S. Pat. No. 7,011,614 issued Mar. 14, 2006, U.S. Pat. No. 6,821,795 issued Nov. 23, 2004, U.S. Pat. No. 7,172,918 issued Feb. 6, 2007, U.S. Pat. No. 7,011,614 issued Mar. 14, 2006, U.S. Pat. No. 7,129,519 issued Oct. 31, 2006 and U.S. Pat. No. 7,351,976 issued Apr. 1, 2008, all in the name of Jose Arno. The disclosures of all such patents are hereby incorporated herein by reference in their entireties, for all purposes.

As discussed in the Background section hereof, the incidence of gas phase nucleation (GPN) and Ti:TiN attack are desirably avoided in the deposition of tungsten on Ti:TiN layers. The present invention resolves this issue by monitoring an effluent gas mixture of the tungsten CVD process, to determine incipient occurrence (onset) of GPN and Ti:TiN attack, and responsively modulate the process conditions of the tungsten CVD process to achieve reduction, and preferably elimination, of such GPN and Ti:TiN attack, in relation to a corresponding tungsten CVD process lacking such monitoring. The invention thereby permits active CVD processing to be carried out with little or no occurrence of GPN and Ti:TiN attack.

Figure 1:
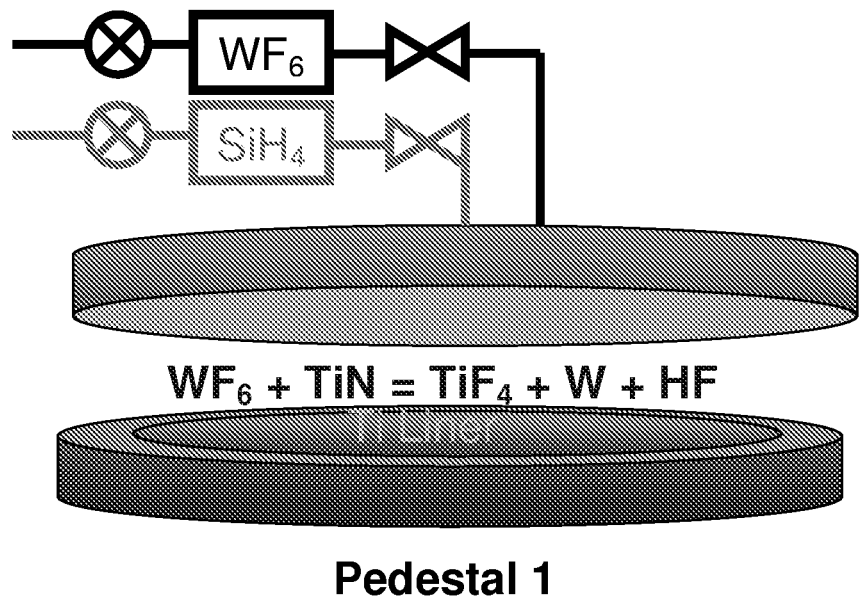
FIG. 1 is a schematic representation of a tungsten CVD process system in which tungsten hexafluoride ($WF_6$) and silane ($SiH_4$) are separately flowed to a deposition chamber including a pedestal having a Ti liner (Ti:TiN layer structure) thereon, wherein the process conditions are such as to favor a Ti attack reaction.

FIG. 1 is a schematic representation of a tungsten CVD process system in which tungsten hexafluoride ($WF_6$) and silane ($SiH_4$) are separately flowed to a deposition chamber including a pedestal having a Ti liner (Ti:TiN layer structure) thereon, wherein the process conditions are such as to favor the Ti attack reaction

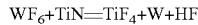

in which $WF_6$ attacks the Ti liner, producing $TiF_4$ and HF as reaction by-products.

Figure 2:
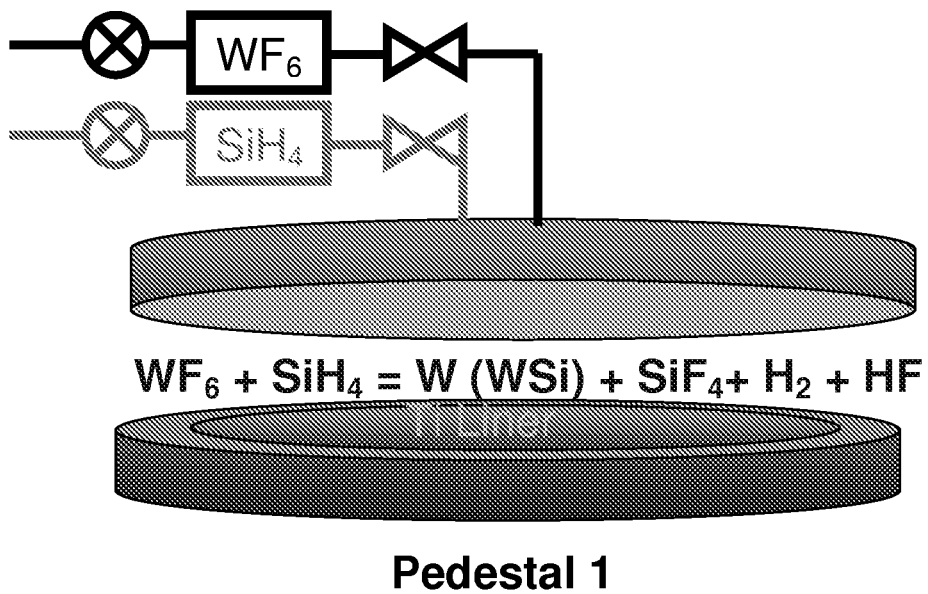
FIG. 2 is a corresponding schematic representation of the tungsten CVD process system of FIG. 1, wherein the process conditions are conducive to occurrence of gas phase nucleation.

FIG. 2 is a corresponding schematic representation of the tungsten CVD process system of FIG. 1, wherein the process conditions have changed to favor the reaction

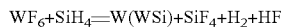

in which gas phase nucleation is taking place, producing tungsten silicide (WSi), $SiF_4$, $H_2$ and HF as reaction by-products.

The operational problem illustrated by the FIG. 1 and FIG. 2 CVD process system conditions is establishing and maintaining the process conditions regime that is free of GPN and Ti liner attack. Such operating regime is difficult to stably maintain, since any significant process condition fluctuations can result in GPN or Ti liner attack occurring. There is thus a fine balance point between GPN and Ti liner attack conditions.

Figure 3:
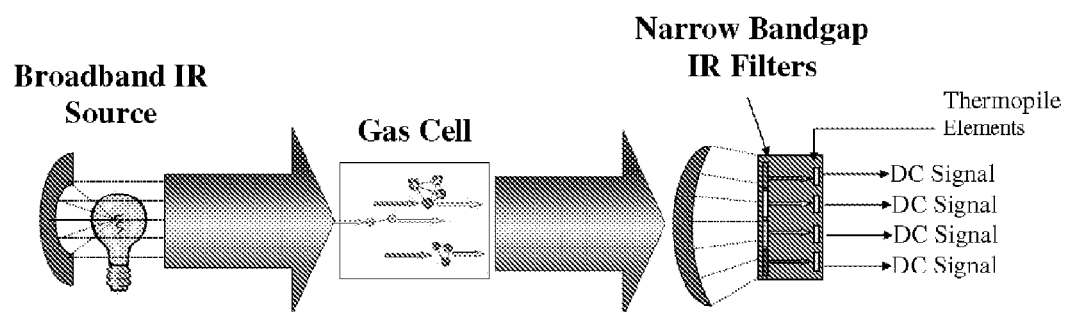
FIG. 3 is a schematic representation of a thermopile infrared (TPIR) detector in which a broadband infrared (IR) source is arranged to transmit IR radiation through a gas cell through which a multicomponent gas mixture is flowed.

FIG. 3 is a schematic representation of a thermopile infrared (TPIR) detector in which a broadband infrared (IR) source is arranged to transmit IR radiation through a gas cell through which a multicomponent gas mixture is flowed. The radiation transmitted through the cell thus interacts with the gas species in the cell in a manner involving reflectance, absorption and scattering of the radiation by the gas species in the gas mixture, resulting in a radiation output from the cell that can then be filtered by narrow bandgap infrared filters to spectral regions of interest for the potential components of the gas mixture. The resultingly filtered radiation then is impinged on TPIR detector elements to produce an output DC signal for each of the spectral regions of interest that is indicative of the presence and concentration of the corresponding gas species producing a radiation-interaction output in that spectral region.

The sensitivity of the TPIR system shown in FIG. 3 may be enhanced by increasing the length of the IR radiation path, e.g., by use of mirrors and/or lenses in arrays providing such increased effective length of the radiation path through the gas mixture in the gas cell.

Figure 4:
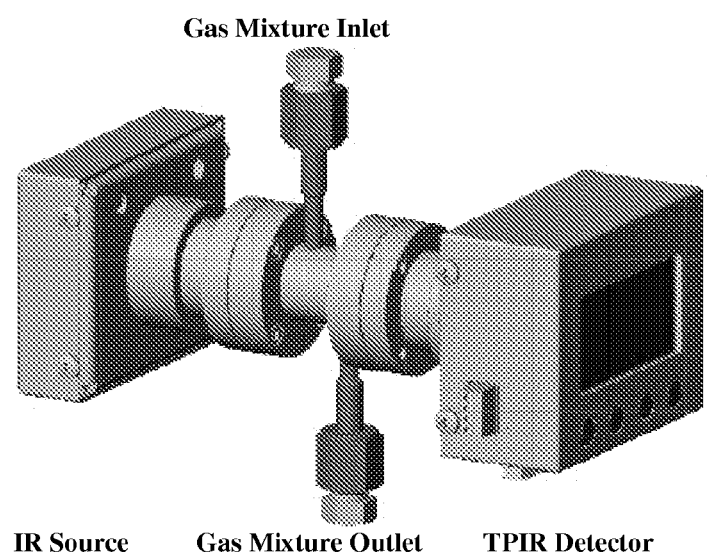
FIG. 4 is a perspective view of a TPIR monitoring apparatus such as may be employed in a tungsten CVD process system in accordance with the invention, in one embodiment thereof.

FIG. 4 is a perspective view of a TPIR monitoring apparatus such as may be employed in a tungsten CVD process system in accordance with the invention, in one embodiment thereof. The monitoring apparatus includes a gas mixture inlet receiving gas mixture from the tungsten CVD system, and a gas mixture outlet for discharging monitored gas mixture for recycling or other disposition in the process system. Intermediate the gas mixture inlet and the gas mixture outlet is a gas cell through which the gas mixture from the CVD system is flowed for interaction with the IR radiation transmitted through the cell.

The IR radiation in the FIG. 4 apparatus is generated from an IR source at an appropriate spectral region of the IR spectrum for the gas mixture component(s) of interest. Opposedly arranged to the IR source is the TPIR detector. Although the TPIR detector in the FIG. 4 apparatus is shown as being in line with the IR source, it will be recognized that other arrangements may be employed in which the TPIR detector is not in linear registration with the IR source, but instead receives output radiation from the gas cell at an other position, by means of an array of mirrors, lenses, etc. situated to direct the output radiation from the gas cell to the detector.

The detector in the TPIR monitoring apparatus of the invention is employed to sense onset of gas phase nucleation or Ti attack conditions and to produce a responsive output for modulating the tungsten CVD process conditions so that occurrence or continuation of GPN or Ti attack is avoided during the tungsten deposition process. For sensing the onset of GPN, the TPIR detector advantageously has a detection capability for particles as small as 0.2 micrometers (μm) in size (diameter).

The detector of the TPIR apparatus is advantageously arranged to monitor the effluent of the CVD process so that the reaction product species resulting from GPN or Ti attack onset is detected in the effluent stream passed through the gas cell, so that a corresponding output is generated to establish, or reestablish, non-GPN and non-Ti attack CVD operation.

The TPIR detector thus provides feedback control of the tungsten CVD system so that CVD operation is maintained in a non-GPN and non-Ti attack regime. The TPIR monitoring apparatus of the invention may additionally be configured to provide end-point monitoring capability for the CVD system, so that an effluent gas composition indicating an endpoint of the CVD process is sensed, and the TPIR apparatus responsively outputs a control signal to terminate the monitoring operation and/or the CVD process.

The TPIR monitoring apparatus is advantageously arranged to monitor the CVD effluent gas stream based on a correlation between effluent characteristics such as concentration and temporal profiles, and GPN or Ti attack events. The chemistry of normal tungsten CVD processing and GPN events is sufficiently different that the TPIR apparatus by monitoring concentration of gas effluent species such as $WF_6$, $SiF_4$ and $SiH_4$ can distinguish such operating states, and generate an output correlative of the specific one of such normal and GPN states that is currently taking place in the CVD system.

The TPIR monitoring apparatus for such purpose may be programmatically arranged to perform a software algorithm in the monitoring operation that will provide an output alarm signal and/or other control signal under GPN conditions.

Corresponding monitoring considerations and arrangements are likewise applicable to Ti attack conditions.

Figure 5:
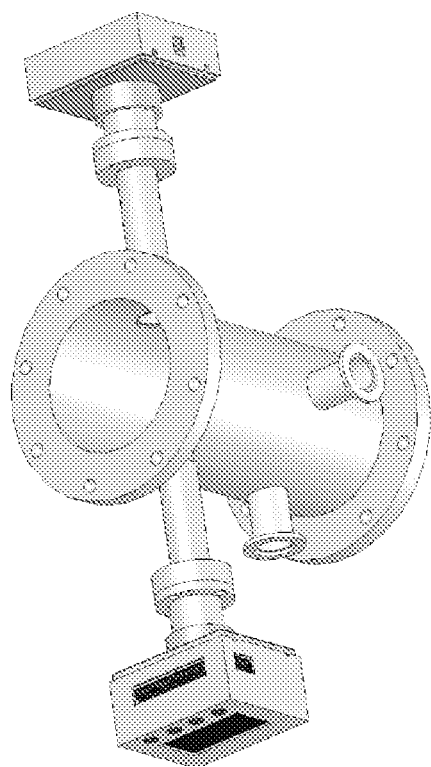
FIG. 5 is a perspective view of a TPIR monitoring apparatus according to another embodiment.

FIG. 5 is a perspective view of the TPIR monitoring apparatus according to another embodiment, showing a central gas cell having flanged ends for coupling with closure members, and radially extending inlet and outlet passages with flanged ends for coupling with the flow circuitry of the CVD system. The IR source is at the upper end of the apparatus, opposite to the TPIR detector assembly module at the lower end of the apparatus, with each of the source and detector components being connected to tubular members that in turn communicate with an interior volume of the gas cell.

The TPIR apparatus in one implementation has a single pass radiation transmission capability with a radiation pathlength of 13 inches on a standard spool piece, installed on a pump line of the CVD system.

Figure 6:
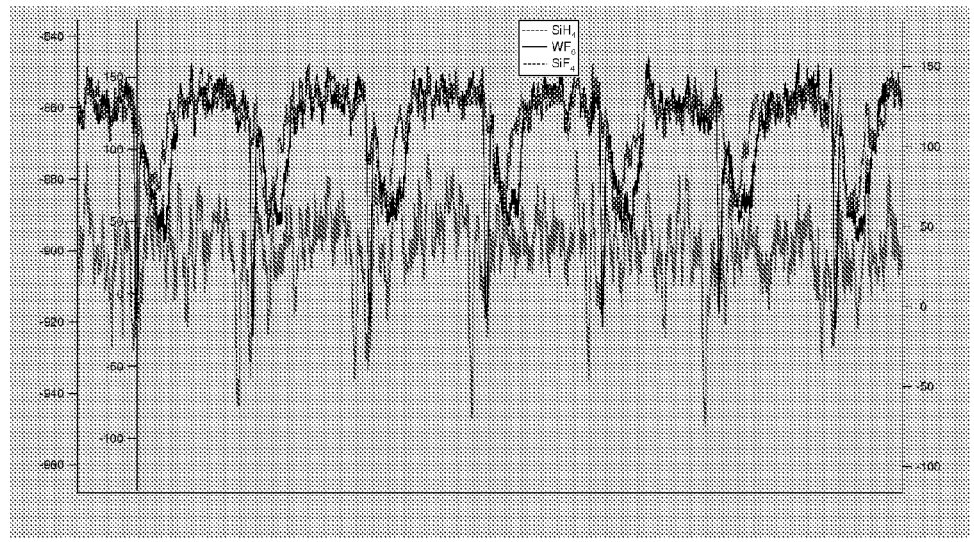
FIG. 6 is a graph of the monitoring output of a TPIR detector arranged for monitoring $WF_6$, $SiH_4$ and $SiF_4$ in a tungsten CVD system, according to one embodiment of the invention.

FIG. 6 is a graph of the monitoring output of a TPIR detector arranged for monitoring $WF_6$, $SiH_4$ and $SiF_4$ in a tungsten CVD system, according to one embodiment of the invention, wherein the top spectral output is $SiF_4$, the intermediate spectral output closely matching the $SiF_4$ output at its peak, but having a deeper trough than the $SiF_4$ output, is $WF_6$, and the bottom spectral output is $SiF_4$.

Figure 7:
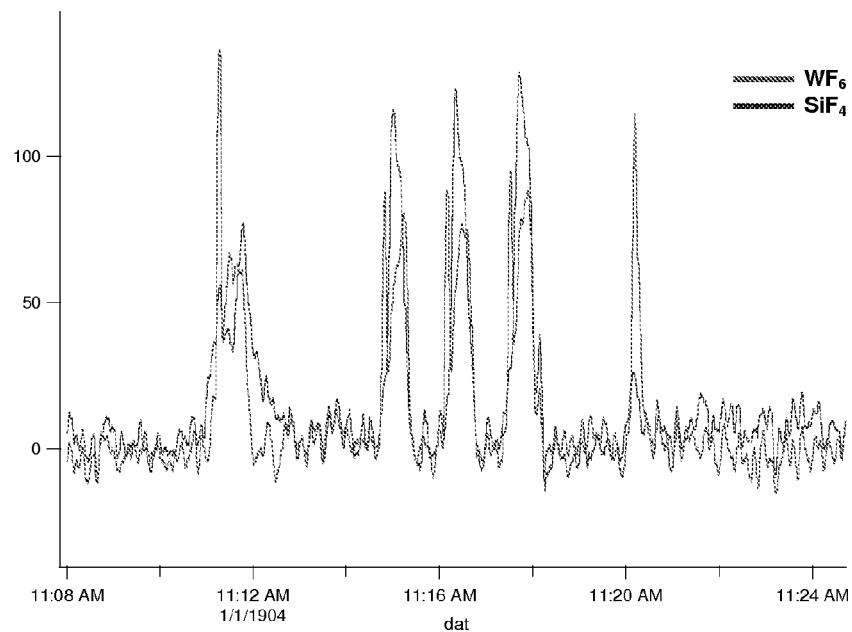
FIG. 7 is a graph of TPIR monitoring apparatus monitoring data for a tungsten CVD system operating with a $SiH_4$ flow rate of 50 sccm and a $WF_6$ flow rate of 300 sccm, and a monitoring system delay of 0.7 seconds.

FIG. 7 is a graph of TPIR monitoring apparatus monitoring data for a tungsten CVD system operating with a $SiH_4$ flow rate of 50 sccm and a $WF_6$ flow rate of 300 sccm, and a monitoring system delay of 0.7 seconds. The spectrum having an output peak above 100 units (arbitrary output scale) at approximately 11:11 AM and shortly after 11:20 AM is the $WF_6$ spectrum, and the spectrum having three peaks above 100 units between 11:14 AM and 11:19 AM is the $SiF_4$ spectrum. These peaks show that the respective spectra are quantitatively sufficient to provide capability for monitoring of GPN conditions.

Figure 8:
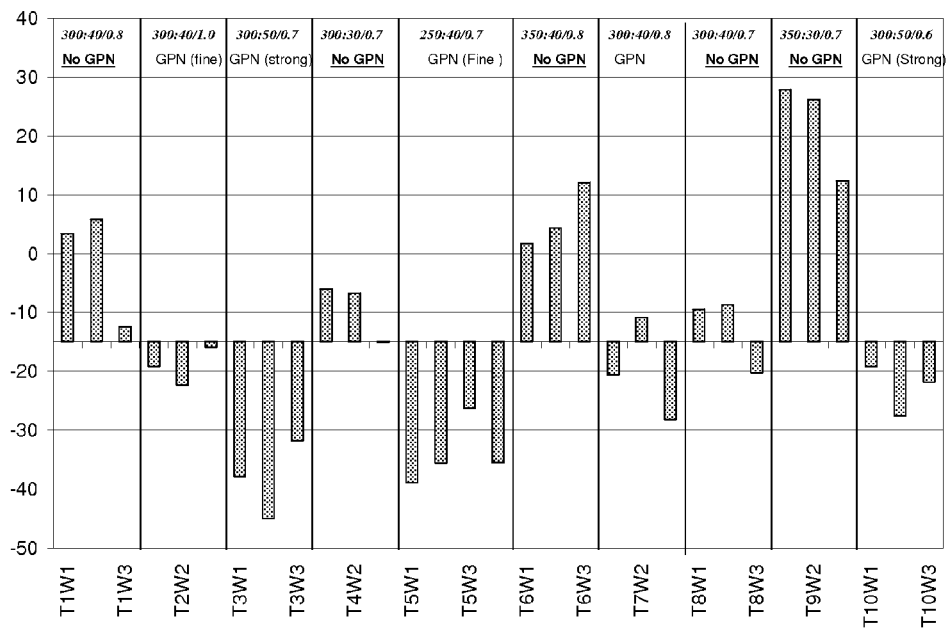
FIG. 8 is a graph of monitoring data from a tungsten CVD system, in which ten different gas mixture recipes were evaluated, with positive sign bars indicate that no GPN was occurring.

In a specific test of a monitoring apparatus of the present invention in a tungsten CVD system, ten different gas mixture recipes were evaluated, with the results shown in FIG. 8. In the FIG. 8 graph, positive sign bars indicate that no GPN was occurring. Eye inspection (EI) determinations were correlated with the data, showing that IR detection was clean in instances in which GPN was clearly visible by EI determination.

These and other empirical results show that GPN is caused by excessive $SiH_4$ or $SiH_4$ being dispensed much earlier than $WF_6$, and that variances in peak height of $SiF_4$ and $WF_6$ can be correlated to GPN. Thus, the timing as well as the concentration of $WF_6$ and $SiH_4$ are critical for GPN. The monitoring operation entails no disturbance of the wafer processing operation, and continuous monitoring is readily carried out.

Figure 9:
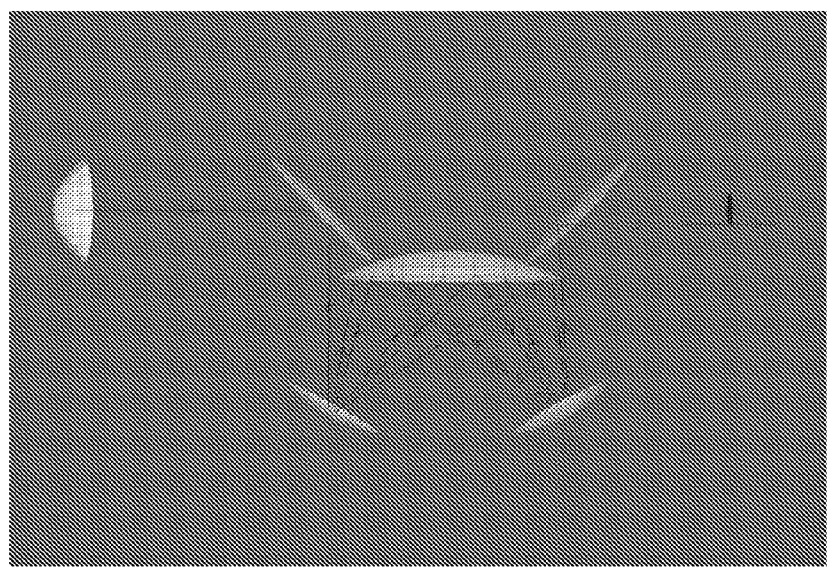
FIG. 9 shows a multi-pass arrangement of mirrors in which the IR source at the left-hand side of the figure emits an IR radiation beam that is reflected multiple times through the gas cell before being passed to the TPIR detector.

In the TPIR monitoring apparatus of the invention, the gas cell can be of a single-pass or a multi-pass character. FIG. 9 shows a multi-pass arrangement of mirrors in which the IR source at the left-hand side of the figure emits an IR radiation beam that is reflected multiple times through the gas cell before being passed to the TPIR detector.

FIG. 10 is a perspective view, and FIG. 11 is a front elevation view, of an in-line multi-pass cell arrangement wherein the monitoring apparatus optics are not exposed directly to the gas flow, and wherein an 8-fold increase in radiation path length is obtained.

FIG. 12 is a graph of wafer processing data for a TPIR monitoring apparatus of the invention, for a 20 wafer lot, including the top $SiF_4$ spectrum, the intermediate $WF_6$ spectrum and the bottom $SiH_4$ spectrum, showing the differentiated character of the three spectra.

Figure 13:
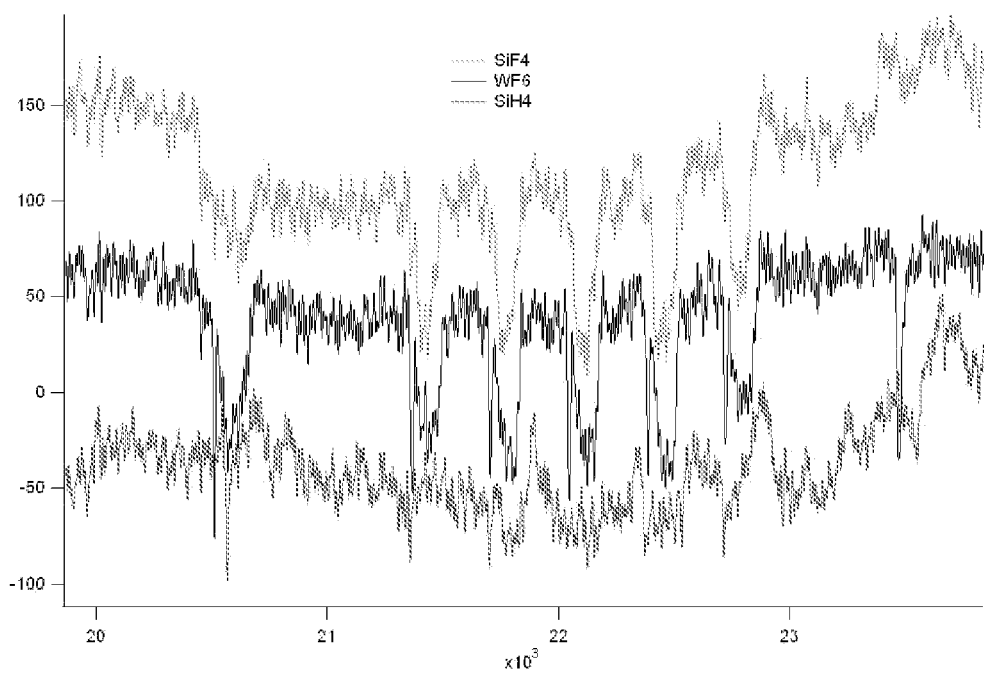
FIG. 13 is a graph of TPIR monitoring data, for a TPIR monitoring apparatus of the invention, with a silane flow rate of 40 sccm, and a tungsten hexafluoride flow rate of 250 sccm, and with a monitoring apparatus delay of 0.7 second, showing the top $SiF_4$ spectrum, the intermediate $WF_6$ spectrum and the bottom $SiH_4$ spectrum.

FIG. 13 is a graph of TPIR monitoring data, for a TPIR monitoring apparatus of the invention, with a silane flow rate of 40 sccm, and a tungsten hexafluoride flow rate of 250 sccm, and with a monitoring apparatus delay of 0.7 second, showing the top $SiF_4$ spectrum, the intermediate $WF_6$ spectrum and the bottom $SiH_4$ spectrum. The data again show the differentiated character of the three spectra.

Figure 14:
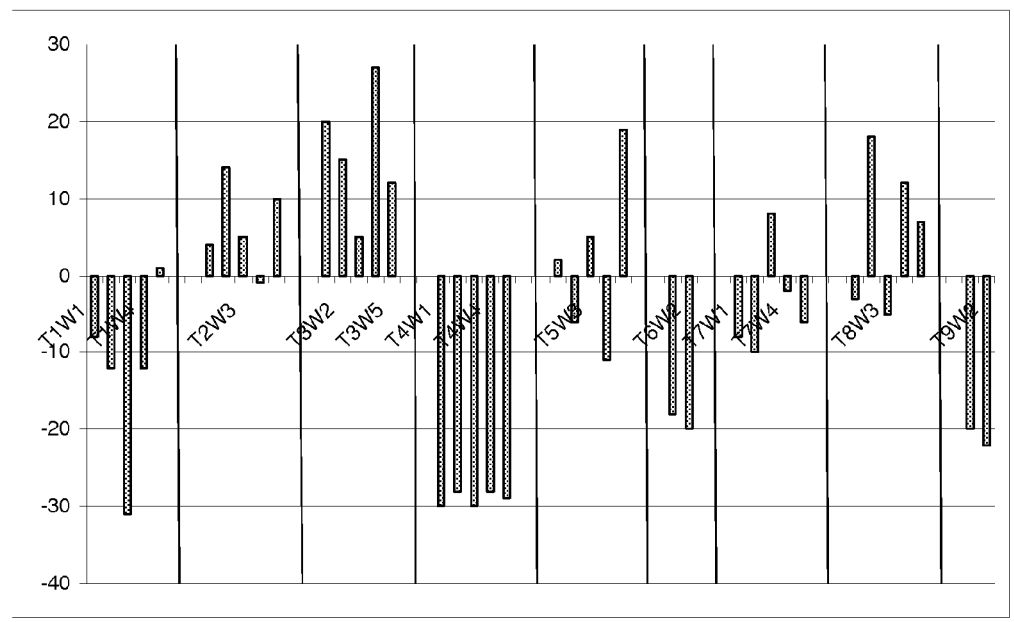
FIG. 14 is a graph of monitoring data from a tungsten CVD system, in which nine different gas mixture recipes were evaluated, with positive sign bars indicate that no GPN was occurring, and negative sign bars indicate that GPN was occurring.

In another test of a monitoring apparatus of the present invention in a tungsten CVD system, nine different gas mixture recipes were evaluated, with the results shown in FIG. 14. In the FIG. 14 graph, positive sign bars indicate that no GPN was occurring, and negative sign bars indicate that GPN was occurring. The data in FIG. 14 show that it is possible to identify strong GPN and non-GPN events.

Empirical testing of TPIR apparatus of the invention show that the $SiH_4$ flowrate and delay time between $SiH_4$ and $WF_6$ delivery are two major factors that cause GPN. The TPIR apparatus of the invention can readily provide accurate measurement of $SiF_4$ and $WF_6$ down to concentrations of 10 parts per million (ppm), and the amount of $SiH_4$ can be correlated to the amount of $SiF_4$ that is produced. Typical delay tuning ranges are from 0.7 to 1.0 second, and accuracy on the order of 0.1 second or less is desired.

Thus, the TPIR apparatus of the invention permits real time monitoring of gas phase nucleation by monitoring gas species ($SiF_4$, $WF_6$, $SiH_4$) in the effluent from the tungsten CVD process. The concentration of these gases as well as their appearance/disappearance rates, and their concentration differences, provide measurements indicative of the types of reactions that are taking place in the CVD chamber of the tungsten CVD system, and an indication of whether or not gas phase nucleation is occurring in the CVD chamber.

Although the foregoing description has been directed to a CVD system arrangement of the TPIR apparatus in which the TPIR apparatus is arranged for monitoring of a pump line for discharging effluent from the CVD system, it will be appreciated that it is possible to arrange the TPIR apparatus for monitoring of gas delivery lines to the CVD chamber, where higher concentrations and more accurate timing can be monitored. For example, the influent $SiH_4$ delivery line to the CVD chamber may be monitored, to provide enhanced detection of silane.

The use of a multi-pass cell between the IR source and IR sensor in the monitoring apparatus of the invention can greatly improve the sensitivity and lower the detection limit of the apparatus. In arrangements in which mirrors are utilized in the TPIR monitoring apparatus and are exposed to the fluid stream in the cell, in a corrosive environment, a corrosion-resistant coating on the mirror, e.g., of nickel or other corrosion-resistant material with good reflectivity characteristics, can beneficially be employed.

Figure 15:
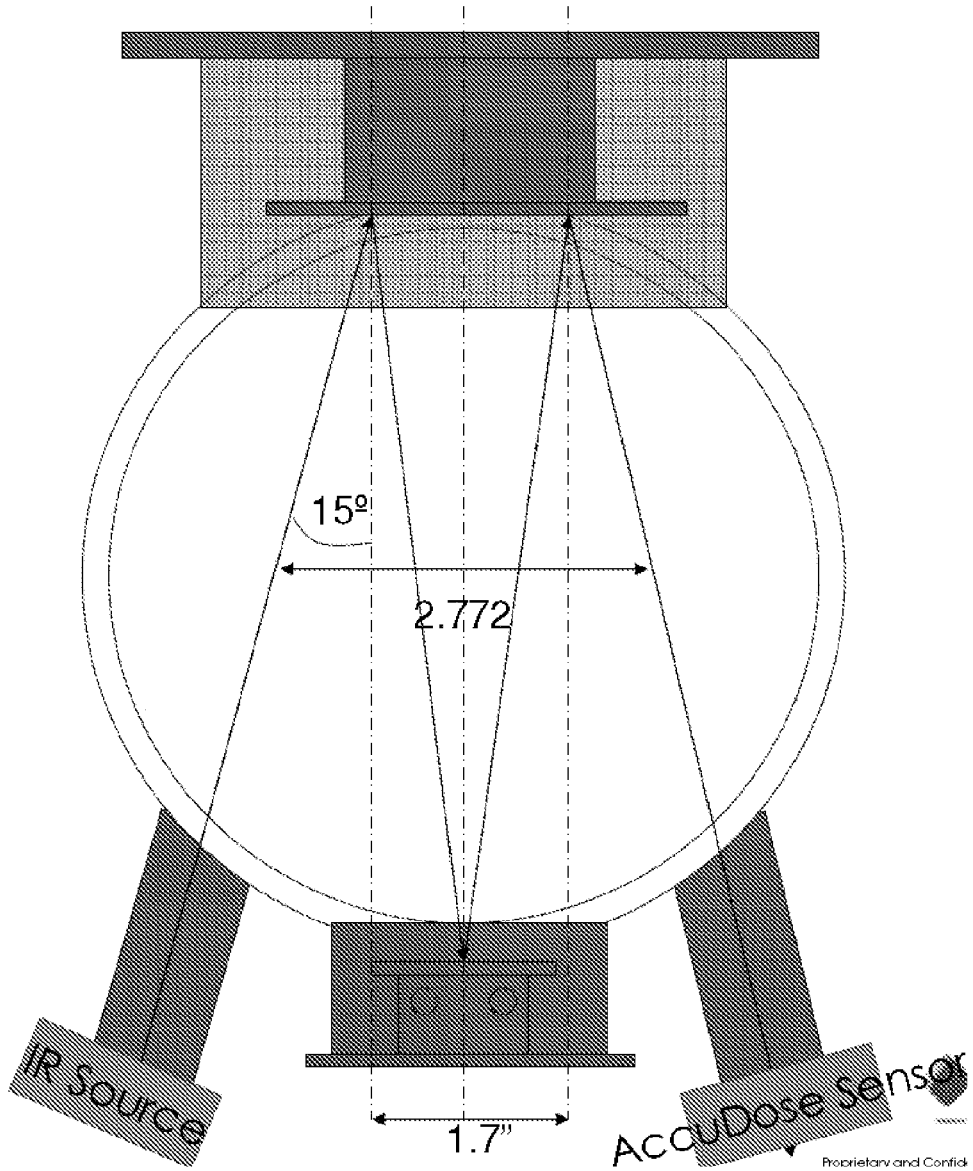
FIG. 15 is a schematic representation of a multi-pass cell according to another aspect of the invention, in which 5 passes of the IR radiation beam is achieved.

FIG. 15 is a schematic representation of a multi-pass cell according to another aspect of the invention, in which 5 passes of the IR radiation beam is achieved. More passes can be obtained in this apparatus by changing the beam angle of the infrared radiation.

Figure 16:
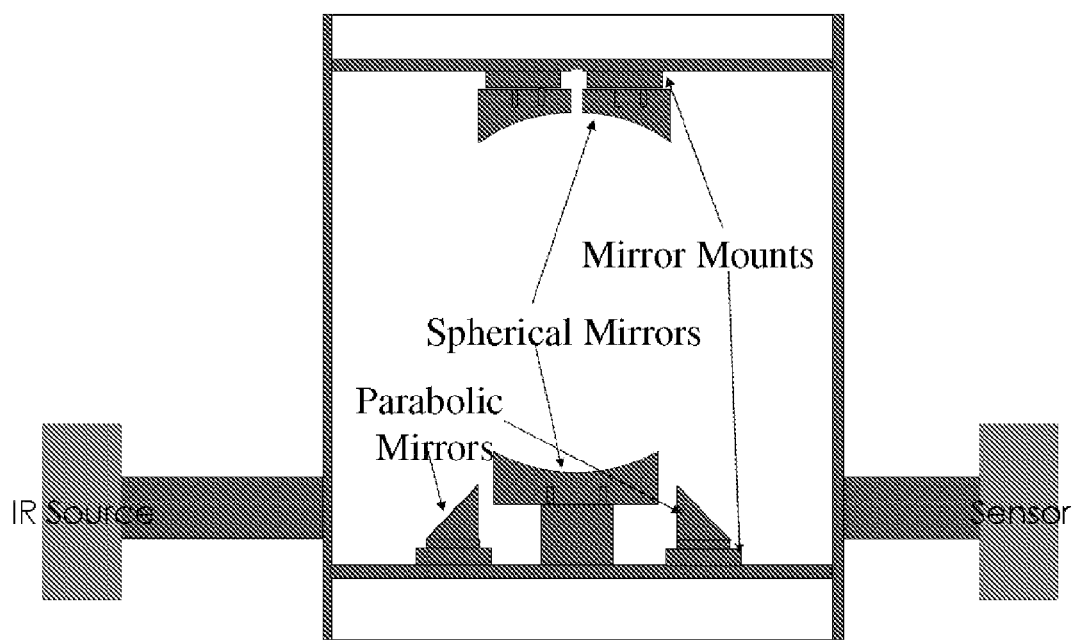
FIG. 16 is a schematic representation of another multi-pass cell arrangement, in which mirrors are mounted inside a cylindrical pipe interposed between an IR source and the TPIR detector (sensor), to provide an extended radiation path length.

FIG. 16 is a schematic representation of another multi-pass cell arrangement, in which mirrors are mounted inside a cylindrical pipe interposed between an IR source and the TPIR detector (sensor), to provide an extended radiation path length.

Figure 17:
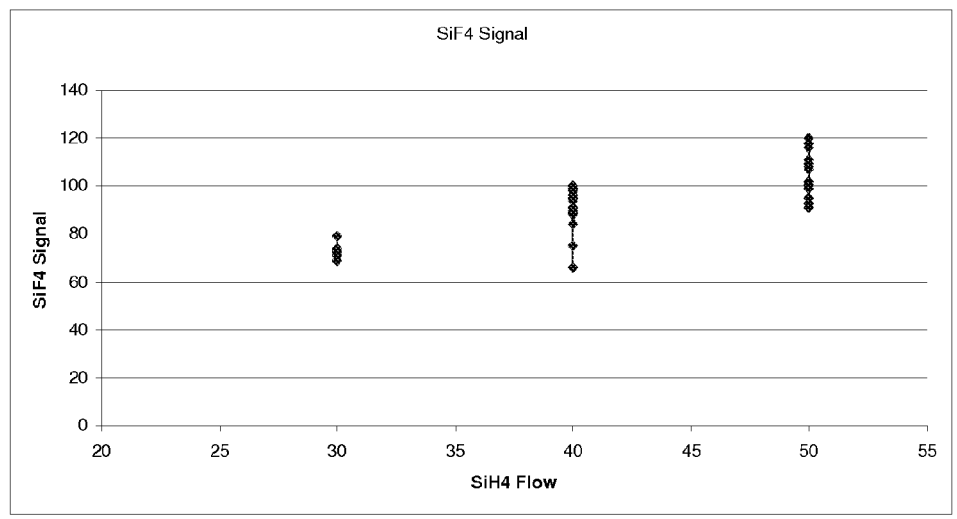
FIG. 17 is a graph of $SiF_4$ signal to $SiH_4$ flowrate, showing the correlation between the two, in a tungsten CVD system including a TPIR monitoring apparatus of the invention.

FIG. 17 is a graph of $SiF_4$ signal to $SiH_4$ flowrate, showing the correlation between the two, in a tungsten CVD system including a TPIR monitoring apparatus of the invention.

Figure 18:
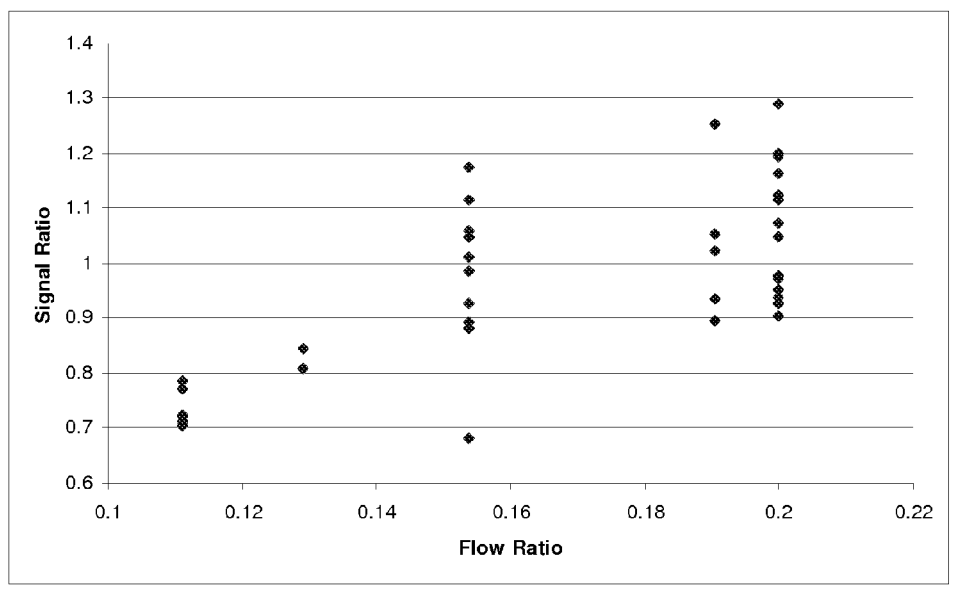
FIG. 18 is a graph of signal ratio of $SiH_4$ signal to $WF_6$ signal, as a function of the ratio of the flowrate of $SiH_4$ to flowrate of $WF_6$, showing the correlation between the two, in a tungsten CVD system including a TPIR monitoring apparatus of the invention.

FIG. 18 is a graph of signal ratio of $SiH_4$ signal to $WF_6$ signal, as a function of the ratio of the flowrate of $SiH_4$ to flowrate of $WF_6$, showing the correlation between the two, in a tungsten CVD system including a TPIR monitoring apparatus of the invention.

The invention contemplates various approaches for algorithmically characterizing the gas species detected by the TPIR apparatus. Such approaches may be implemented by a central processing unit, such as a programmable logic controller, microprocessor, computer or server including a memory or other data carrier that contains a program, firmware or the like, that is executable to carry out the algorithmic detection of the gas species of interest in the gas being sampled by the TPIR apparatus. The gas species can include source materials, reactants, reaction products or other species in the stream being monitored by the TPIR apparatus. Such specially adapted machine may be embodied in a module containing the TPIR detector, e.g., of a type shown in FIG. 5 hereof.

Although the invention is primarily described herein in application to a gas stream containing one or more gas species of interest, it is to be recognized that the invention is not thus limited in applicability, and that the invention may be employed for monitoring other species such as liquid components and/or solid components, or of gas and/or liquid and/or solid components of a stream containing same. In the same respect, other forms of materials, e.g., plasma species, adsorbed species, nanoparticulate composite materials, etc. may be monitored using the apparatus and method of the invention.

Figure 19:
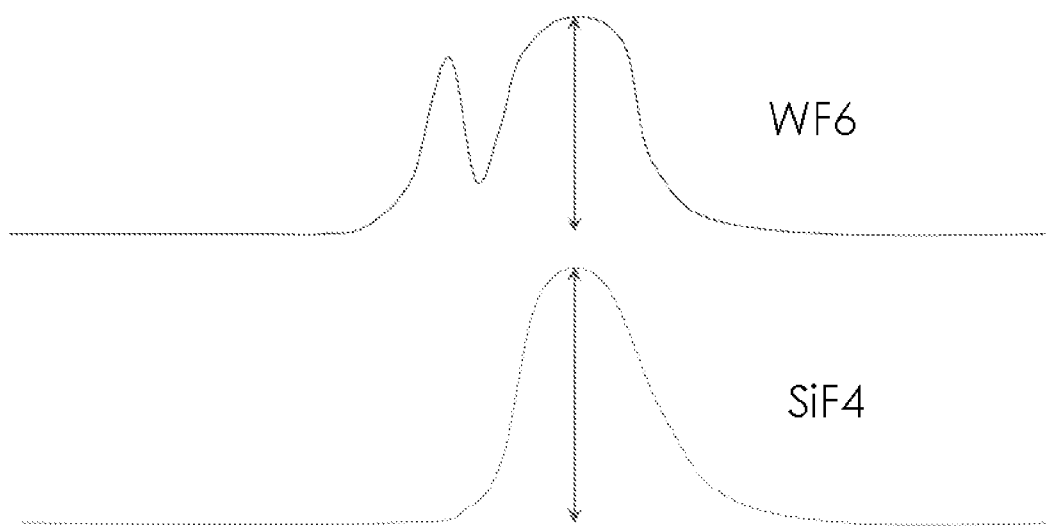
FIG. 19 includes spectra of $WF_6$, and $SiF_4$, illustrating detection of onset of GPN and/or Ti attack in a gas stream containing silicon tetrafluoride ($SiF_4$) and $WF_6$, with a TPIR monitoring apparatus programmably arranged to detect peak heights of these components in the radiation output spectra of the monitoring cell.

In one aspect, directed to detection of onset of GPN and/or Ti attack in a gas stream containing silicon tetrafluoride ($SiF_4$) and $WF_6$, the TPIR monitoring apparatus may be programmably arranged to detect peak heights of these components in the radiation output spectra of the monitoring cell, as illustrated in the spectra of $WF_6$, and $SiF_4$ in FIG. 19 hereof.

By measuring the peak heights, $H_{WF6}$ and $H_{SiF4}$, of $SiF_4$ and $WF_6$ in such monitoring operation, the monitoring apparatus is able to predict GPN and/or Ti attack. Such prediction can also be derived by determining a peak height difference ($H_{WF6}-H_{SiF4}$), or a peak height ratio ($H_{WF6}/H_{SiF4}$) of $SiF_4$ and $WF_6$ to determine onset conditions for GPN and/or Ti attack.

Figure 20:
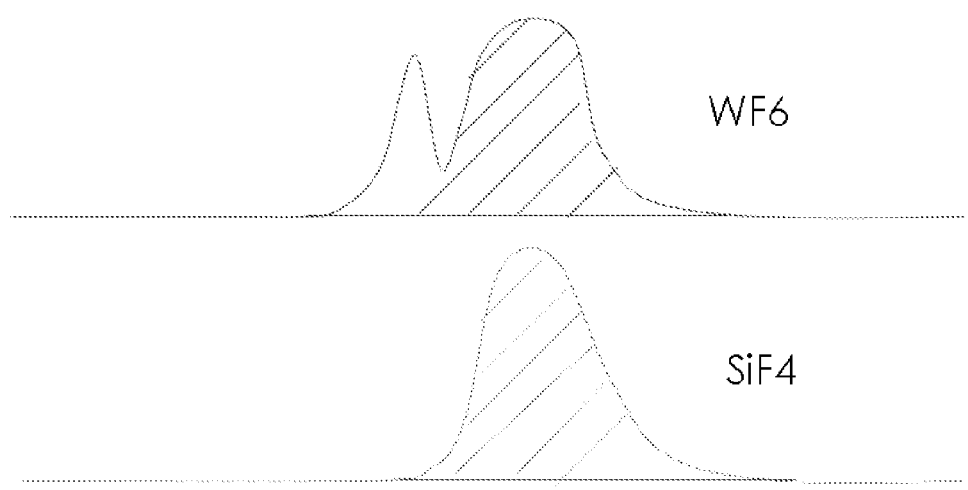
FIG. 20 includes spectra of $WF_6$, and $SiF_4$, illustrating detection of onset of GPN and/or Ti attack in a gas stream containing silicon tetrafluoride ($SiF_4$) and $WF_6$, with a TPIR monitoring apparatus programmably arranged to detect peak areas of the spectral curves of these components in the radiation output of the monitoring cell.

In another aspect, directed to detection of onset of GPN and/or Ti attack in a gas stream containing silicon tetrafluoride ($SiF_4$) and $WF_6$, the TPIR monitoring apparatus may be programmably arranged to detect peak areas of the spectral curves of these components in the radiation output of the monitoring cell, as in the spectra of these components shown in FIG. 20 hereof.

By measuring the peak areas (area under the curve, or AUC) of $SiF_4$ and $WF_6$ in such monitoring operation, the monitoring apparatus is able to predict GPN and/or Ti attack. Such prediction can also be derived by determining an AUC difference ($AUC_{SiF4}-AUC_{WF6}$) or an AUC ratio ($AUC_{SiF4}/AUC_{WF6}$) of $SiF_4$ and $WF_6$ to determine onset conditions for GPN and/or Ti attack.

Figure 21:
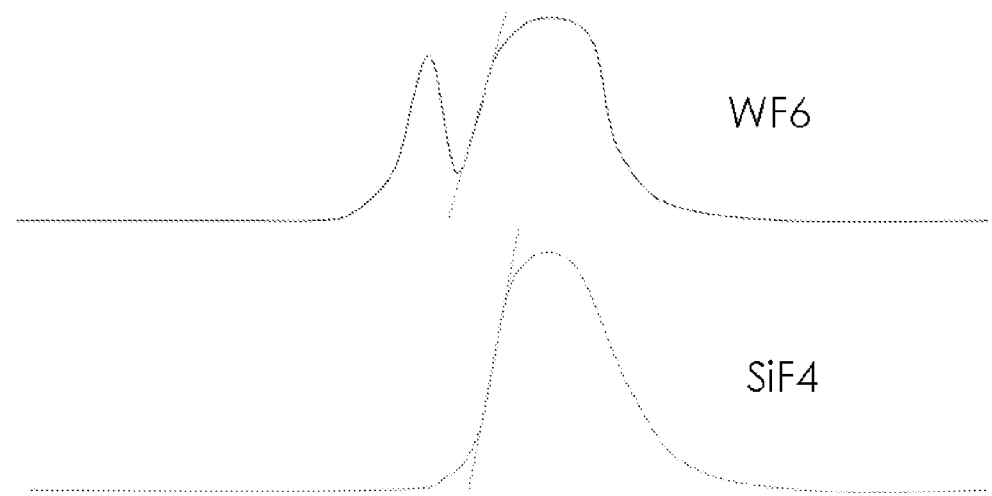
FIG. 21 includes spectra of $WF_6$, and $SiF_4$, illustrating detection of onset of GPN and/or Ti attack in a gas stream containing silicon tetrafluoride ($SiF_4$) and $WF_6$, with a TPIR monitoring apparatus programmably arranged to determine the slope, S, of the spectral curves of these components ($S_{SiF4}$ and $S_{WF6}$) in the radiation output of the monitoring cell.

In a further aspect, directed to detection of onset of GPN and/or Ti attack in a gas stream containing silicon tetrafluoride ($SiF_4$) and $WF_6$, the TPIR monitoring apparatus may be programmably arranged to determine the slope, S, of the spectral curves of these components ($S_{SiF4}$ and $S_{WF6}$) in the radiation output of the monitoring cell, as illustrated in the spectra of these components shown in FIG. 21 hereof.

By measuring the slopes of the curves of $SiF_4$ and $WF_6$ spectra in such monitoring operation, the monitoring apparatus is able to predict GPN and/or Ti attack. Such prediction can also be derived by determining a difference in slopes ($S_{SiF4}-S_{WF6}$) or a slope ratio ($S_{SiF4}/S_{WF6}$) of $SiF_4$ and $WF_6$ to determine onset conditions for GPN and/or Ti attack.

Slopes of the $WF_6$ and $SiF_4$ spectral curves can be usefully employed because they reflect the reaction rate of the tungsten CVD process, and the spectral curves of these components for GPN conditions are typically quite different from the spectral curves obtained under conditions of normal (GPN-free and Ti attack-free) deposition of tungsten on the wafer surface.

Figure 22:
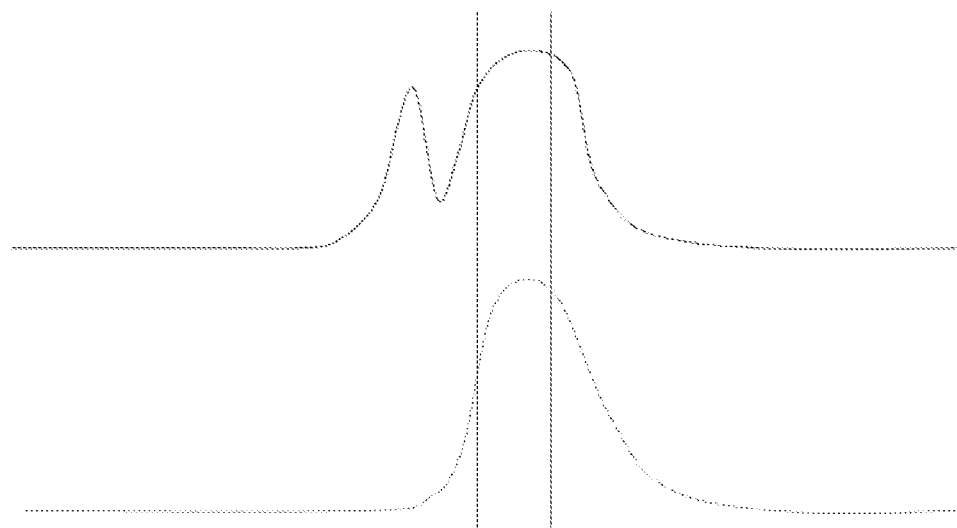
FIG. 22 includes spectra of $WF_6$, and $SiF_4$, illustrating detection of onset of GPN and/or Ti attack in a gas stream containing silicon tetrafluoride ($SiF_4$) and $WF_6$, with a TPIR monitoring apparatus programmably arranged to monitor peak heights at any specific point in time, rather than simply the amplitude of the peaks.

In yet another aspect, directed to detection of onset of GPN and/or Ti attack in a gas stream containing silicon tetrafluoride ($SiF_4$) and $WF_6$, the TPIR monitoring apparatus may be programmably arranged to monitor peak heights at any specific point in time, rather than simply the amplitude of the peaks, as shown in the $WF_6$ (top curve) and $SiF_4$ (bottom curve) spectral curves in FIG. 22. Such monitoring of peak heights at a specific time can be quite useful in determining onset of GPN and/or Ti attack, since relative concentrations of the gases may change at any point in the process and cause GPN or Ti attack.

The temporal traces of the peaks of $WF_6$ and $SiF_4$ spectral curves also reflect the timing of the gas dispense, which is another factor that can cause GPN and/or Ti attack.

Thus, a "time slice" of the spectrum (AH) may be obtained for each of the $WF_6$ and $SiF_4$ spectral curves, and used independently, or aggregately (e.g., as differences or ratios), to determine correlates of the onset of GPN and/or Ti attack.

Figure 23:
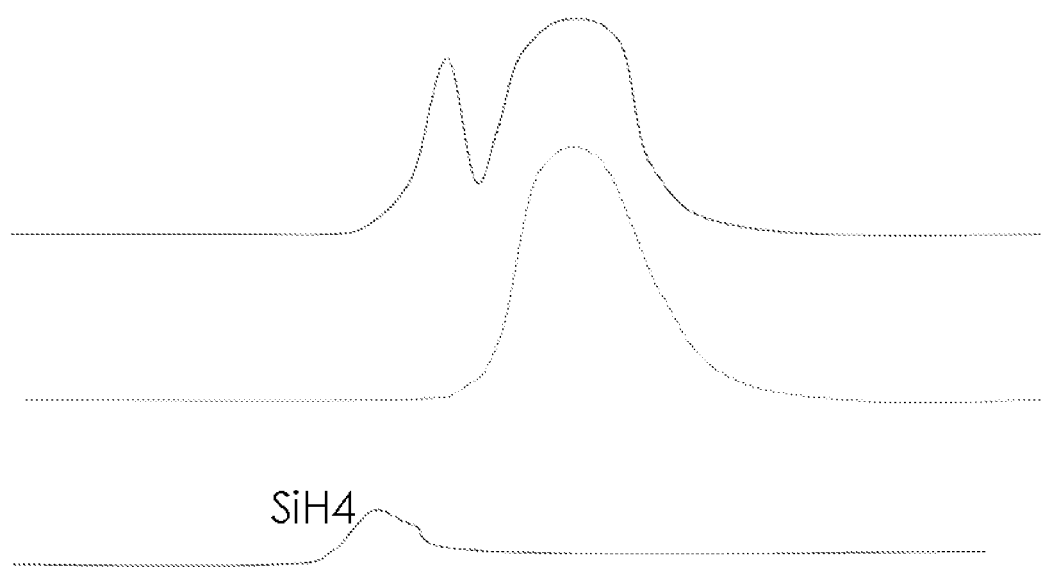
FIG. 23 is a TPIR monitoring apparatus output, as employed for detection of onset of GPN and/or Ti attack during tungsten CVD.

In a still further aspect, directed to detection of onset of GPN and/or Ti attack in a gas stream containing silicon tetrafluoride ($SiF_4$) and $WF_6$, the TPIR monitoring apparatus may be programmably arranged to monitor silane ($SiH_4$), as in the spectral curves (top curve $WF_6$, middle curve $SiF_4$, and lower curve $SiH_4$) shown in FIG. 23.

This monitoring mode is based on the fact that $SiH_4$ is typically completely consumed during tungsten CVD. Any residual $SiH_4$ therefore can be utilized as an indicator of GPN and/or Ti attack.

Note that in the implementation of the foregoing monitoring arrangements, it may be desirable to construct the monitoring detection module, e.g., as shown at the lower portion of the apparatus illustrated in FIG. 5, so that it incorporates as part of the module a CPU providing an output signal for modulating the CVD process to suppress or eliminate GPN and/or Ti attack. Such CPU may usefully incorporate or be communicatively coupled with a database including spectra or spectral characteristics of onset of GPN and Ti attack, against which current monitoring spectra or spectral characteristics can be matched or otherwise correlated or processed, for purposes of determining if onset of GPN or Ti attack is currently occurring, and if such GPN or Ti attack is incipient, then providing a output for modulation of the CVD process to avoid such GPN or Ti attack behavior.

The output and resulting modulation of the CVD process may involve any suitable changes of process conditions, e.g., pressure, temperature, flow rate and composition of gases or individual gas species flowed to the process chamber. Thus, in application to tungsten CVD, the relative flow rates of silane and tungsten hexafluoride may be adjusted in response to the monitoring sensing of the output radiation from the sampling cell, so that the gas phase constitution of the gas mixture in the deposition chamber is not conductive to GPN or Ti attack, so that normal operation may be maintained throughout the deposition process.

The modulation of the process system to suppress and avoid GPN and Ti attack conditions may be carried out in any suitable manner, using conventional signal processing, transmission and control components, including for example flow control valves and valve actuator assemblies, pressure transducers, thermocouple sensors, etc., within the skill of the art, based on the disclosure herein.

The TPIR monitoring system of the present invention in another aspect embodies a system and algorithms for data analysis, to increase the resolution of the monitoring operation and control of the process system to avoid GPN and Ti attack conditions.

The TPIR monitor utilizes a hot filament infrared source and a thermopile infrared detector. Due to the character of the thermopile detector, as functioning to measure temperature change, the infrared detector is sensitive not only to incident infrared light but also to ambient temperature changes in the environment of the CVD process. Additionally, white noise from ambient light and electronics, such as power supplies, also operate to potentially adversely affect the signal-to-noise level in the infrared monitoring operation.

The present invention in such additional aspect therefore utilizes an algorithmic approach for calibrating signals from the TPIR monitoring system, which may be implemented by a monitoring and control system programmably arranged to carry out the monitoring, data analysis, and control functions, using the data analysis algorithm, e.g., as contained in a memory unit, such as a RAM, ROM, PROM device in which the data analysis algorithm and associated monitoring and control operational instructions are stored, which may be associated with a processor and other components of a monitoring and control system, wherein the processor is arranged to access and execute the data analysis algorithm and associated monitoring and control operational instructions. Alternatively, the data analysis algorithm and associated monitoring and control operational instructions may be stored on a computer-readable medium, such as a disc, memory stick, or other data carrier device, to be used in a computer system adapted to carry out the monitoring, data analysis and control functions stored on the data carrier device.

It will be appreciated that any of the methods and techniques described hereinabove or hereafter for TPIR monitoring and/or control are contemplated as being likewise able to be implemented within the broad practice of the invention as above described, e.g., by memory units and/or data carrier devices, with associated processors and other components of a monitoring and control system.

This algorithmic approach for calibrating signals from the TPIR monitoring system is illustrated below with respect to an exemplary application.

Figure 24:
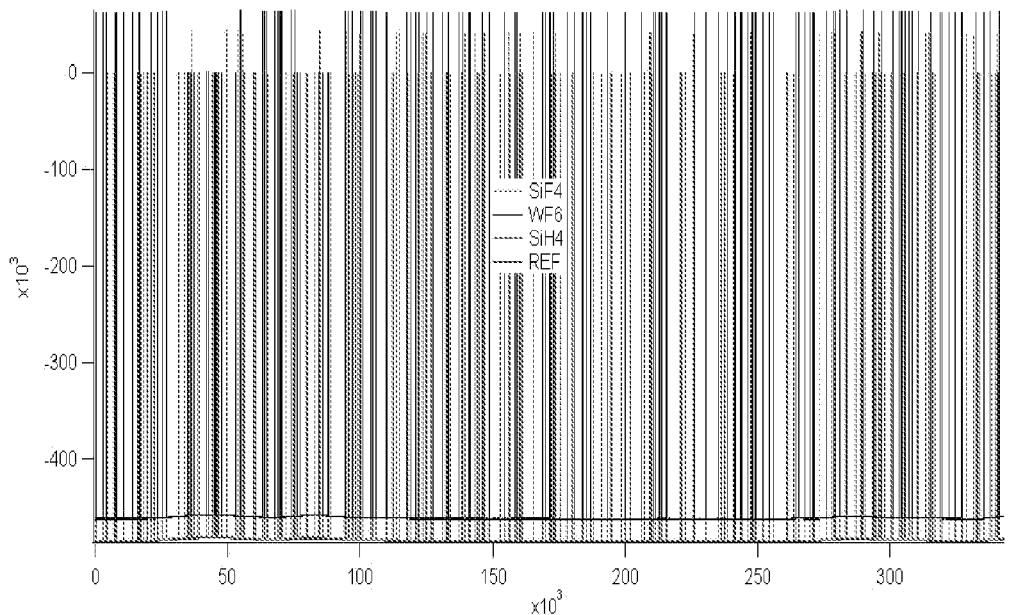
FIG. 24 is a TPIR monitoring system output for a 4-channel detector, including a reference channel and channels for silicon tetrafluoride, tungsten hexafluoride and silane.
Figure 25:
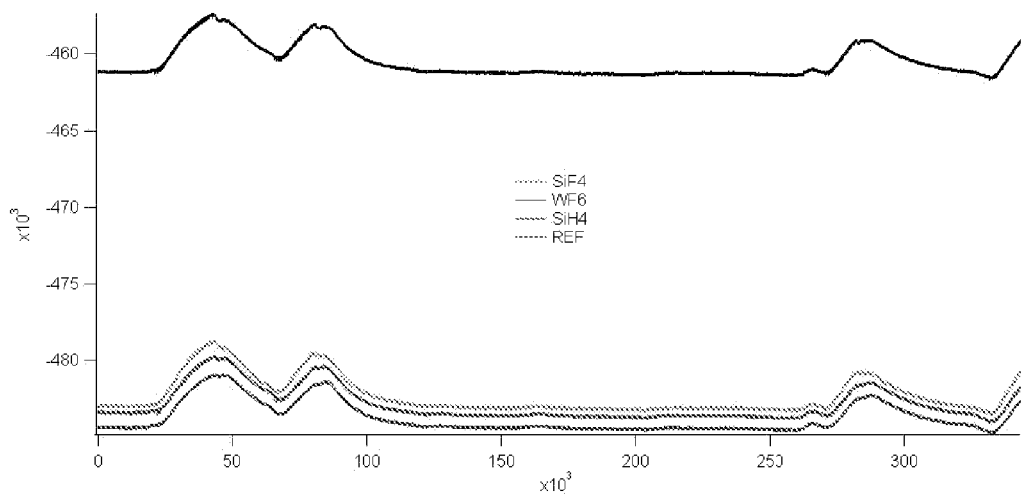
FIG. 25 is a graph of the output of the TPIR monitoring system of FIG. 24, with the spikes removed.

The radiation output signal of the monitoring cell may have spikes due to ambient radio frequency noise. Such ambient noise can be readily removed, since most of the spikes are significantly larger than the fundamental monitoring signal. FIG. 24 shows a graph of raw data for a radiation output signal of a monitoring cell in a CVD process system, and FIG. 25 shows the corresponding signal output with the spikes removed. The output signals include spectra for silicon tetrafluoride, tungsten hexafluoride, silane and a reference signal ("REF").

The corresponding code for the spike removal process is as follows:

```
Code:
If (Signal (n)>-40000)
    Then Signal (n) = Signal (n-1)
```

After such removal of spikes from the output, the data are still noisy, primarily because of so-called "short noise" from the associated electronics of the monitoring and CVD process systems. To smooth the data, a binomial smoothing algorithm is employed with a smoothing term of 50. The corresponding code is:

```
Code:
Smooth_binomial_n_50 (Signal)
```

Figure 26:
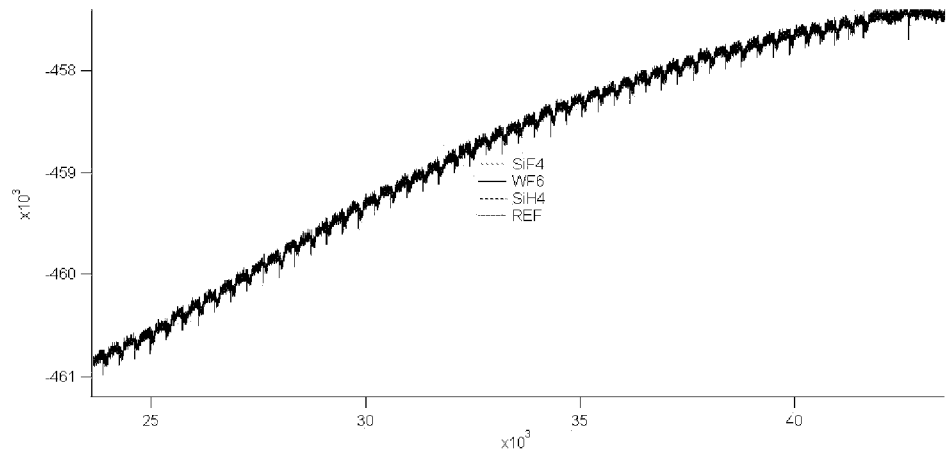
FIG. 26 is a TPIR output for the 4-channel TPIR monitoring system of FIGS. 24 and 25, prior to data smoothing.
Figure 27:
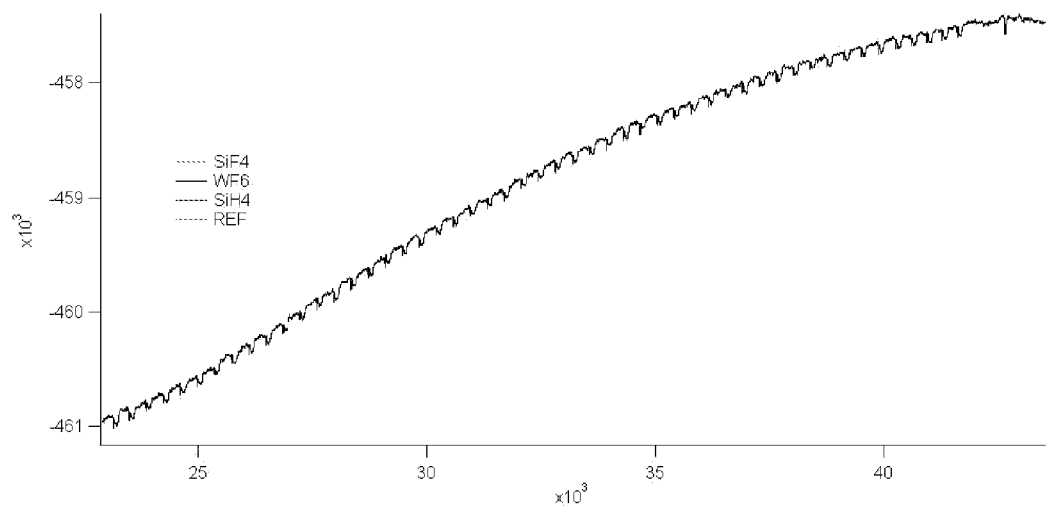
FIG. 27 is a graph of TPIR monitoring system output, for the data of FIG. 26, after data smoothing.

This data smoothing operation was employed to smooth the data shown in FIG. 26, with the corresponding smoothed data being shown in FIG. 27, for the same spectral components and reference shown in FIGS. 24 and 25 (silicon tetrafluoride, tungsten hexafluoride, silane and "REF" reference signal).

As indicated, the TPIR detector is sensitive to ambient temperature change, and temperature corrective operations are advantageously employed to compensate for such variable temperature. The ambient temperature can introduce large baseline change of the output signal of the monitoring cell, and render subsequent analysis difficult. The TPIR may, for example, have four channels, for the illustrative case of monitoring of silicon tetrafluoride, tungsten hexafluoride and silane, together with a reference channel, wherein the reference channel is employed to calibrate the remaining chemical reagent channels.

The ambient temperature change experienced by the TPIR monitoring system should introduce a same trend of signal changes on all four channels of the detector. Insofar as detector settings remain the same, signal changes on channels 2, 3 and 4 (silicon tetrafluoride, tungsten hexafluoride and silane, respectively) should be proportional to channel 1 (the reference channel). If the slopes and offsets of channels 2, 3 and 4 are calculated against channel 1, then the results can be employed for temperature correction of the monitoring system. The corresponding code is as follows:

```
Code:
Plot Ch2, 3, 4 vs. Ch1
Linear Fit Ch2, Ch3, Ch4 vs. Ch1
Output (a2, b2; a3, b3; a4, b4) (wherein a2, a3, a4 are slopes and b2, b3, b4 are offsets)
``` wherein Ch=channel.

Figure 28:
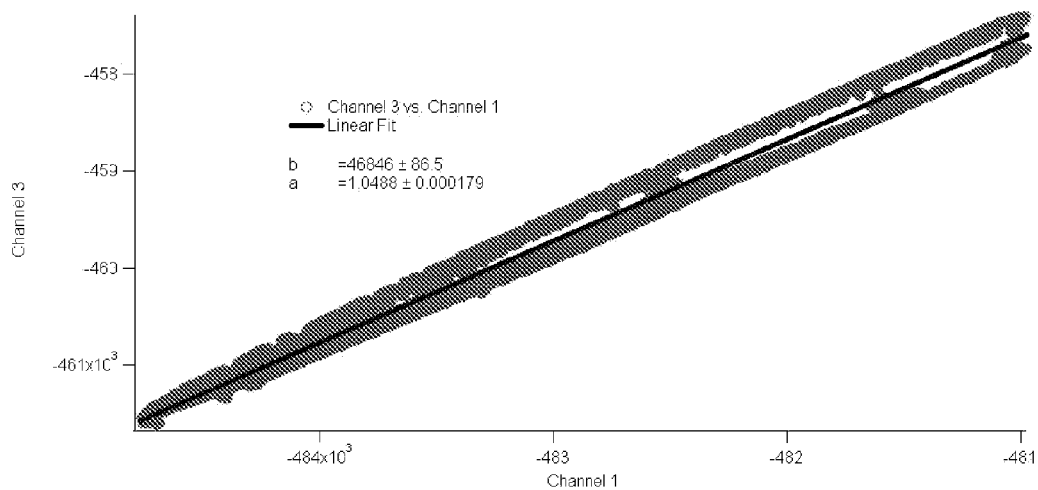
FIG. 28 is a graph of linear fitting of channel 3 to channel 4 in a 4-channel TPIR monitoring system, for calculation of slope and offset.

FIG. 28 illustrates a linear fitting of channel 3 to channel 1 to calculate slope and offset.

Next, temperature correction is effected, utilizing the following code:

Code:

$$Ch2=Ch2-a2*Ch1-b2$$

$$Ch3=Ch3-a3*Ch1-b3$$

$$Ch4=Ch4-a2*Ch1-b4$$

Figure 29:
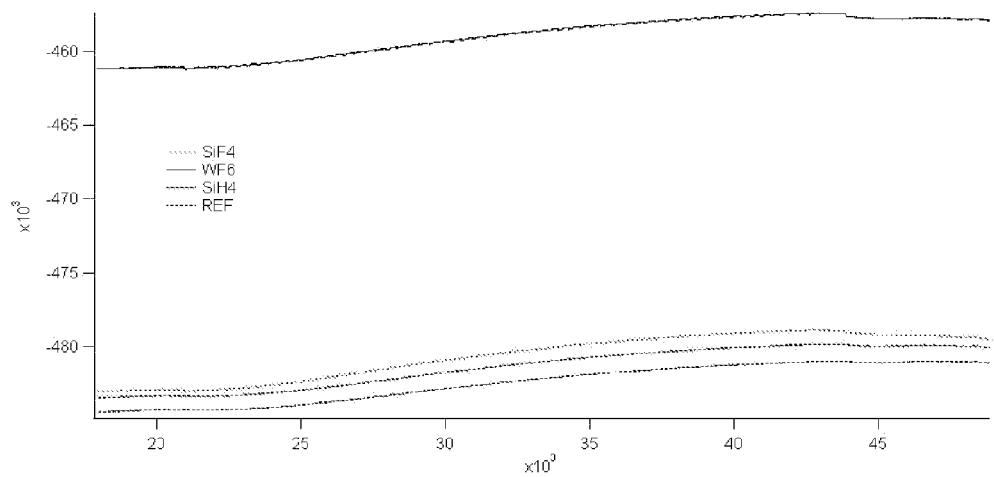
FIG. 29 is an output of a TPIR monitoring system prior to temperature correction.
Figure 30:
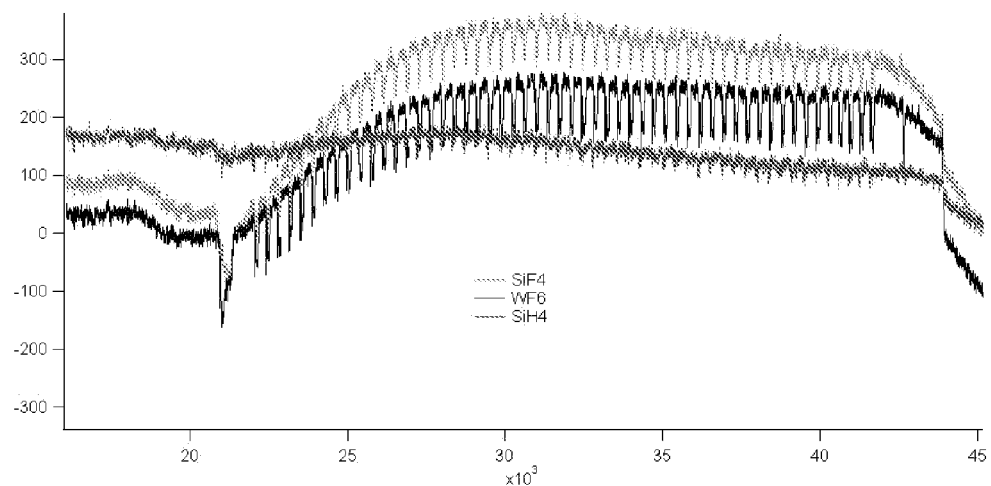
FIG. 30 is a graph of output of the TPIR monitoring system for which data appears in FIG. 29, after temperature correction of such data.

FIG. 29 shows a plot of the spectra for the four channels before temperature correction. FIG. 30 shows the corresponding spectra after temperature correction. It is seen that the baseline still has some curvature after temperature correction, but such curvature should not affect further data analysis.

In order to extract meaningful information from the data, peaks of silicon tetrafluoride and tungsten hexafluoride corresponding to CVD processing of each individual wafer have to be identified. The location of the peak for the wafer can be accomplished utilizing any suitable peak search algorithm. For example, a simple peak search algorithm can be used involving the histogram of Signal(n+A)−Signal(n) where A is the pre-defined parameter. Either channel 2 (silicon tetrafluoride) or channel 3 (tungsten hexafluoride) can be used for the search. The corresponding code is as follows:

```
Code:
Num_peak = 0
A = 100
Peak_threshold = 50
For (I = 0 to Num_Data_Points−A)
    If (Signal (I+A)−Signal(I) > Peak_threshold)
        Num_peak = Num_peak + 1
        Peak_Position = I+A
    Endif
EndFor
```

Figure 31:
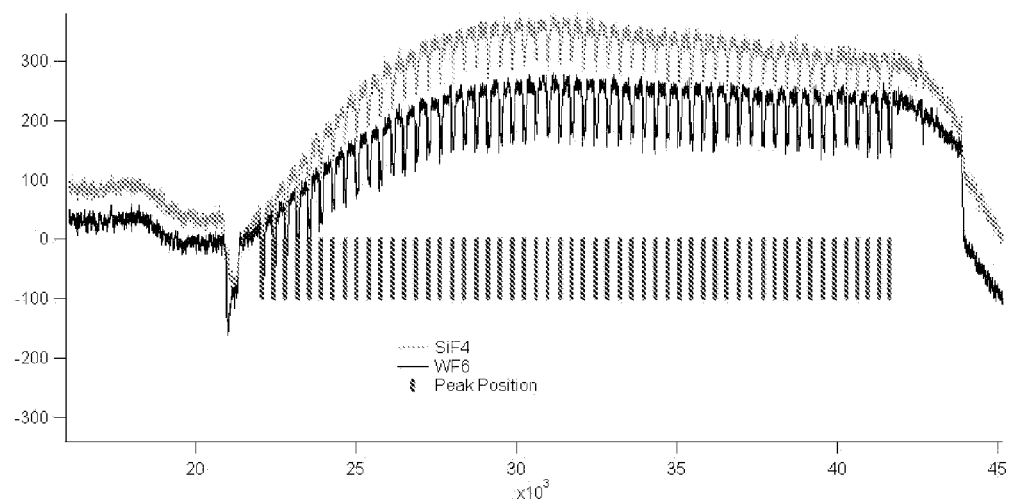
FIG. 31 is a graph of output spectra for a tungsten CVD system, showing peak search results obtained by searching a tungsten hexafluoride signal.

A graph of the peak search results obtained by searching the tungsten hexafluoride signal is shown in FIG. 31.

Peak height of silicon tetrafluoride and tungsten hexafluoride then is calculated by a minimum search. Because the baseline may sometimes still retain curvatures, it is necessary to do a baseline correction to obtain correct peak heights. The corresponding code is as follows:

Code:

> Range=70
>
> Left_limit=80
>
> Right_limite=80
>
> Base_range=50
>
> Peak_height=Max(Peak_position−range, Peak_position+range)
>
> Base_left=Average(Peak_position−left_limit−base_range, Peak_position−left_limit+base_range)
>
> Base_right=Average(Peak_position−right_limit−base_range, Peak_position−right_limit+base_range)
>
> Peak_height=Peak_height−½(Base_left+Base_right)

Figure 32:
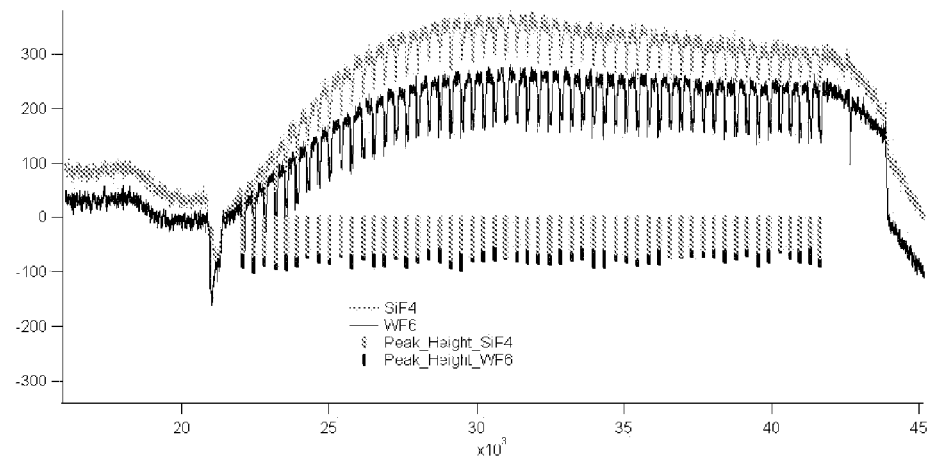
FIG. 32 is a graph of TPIR monitoring system output, showing peak heights of silicon tetrafluoride and tungsten hexafluoride.

A resulting graph of peak heights of silicon tetrafluoride and tungsten hexafluoride are shown in FIG. 32.

After peak heights are extracted from the TPIR monitoring system data, the system can determine whether or not to output a GPN warning based on the difference of the silicon tetrafluoride and tungsten hexafluoride signals. Typically, if the $SiF_4$ signal is larger, it means that silane is in excess and GPN is very likely to occur under such conditions. Accordingly, a warning or termination of wafer processing is necessary. The corresponding code for such operation is as follows:

```
Code:
Warning_Flag = 0
If (Peak_SiF4 − Peak_WF6 < 0) (Keep in mind, all the peak heights are
negative)
Warning_Flag = 1
Endif
```

Figure 33:
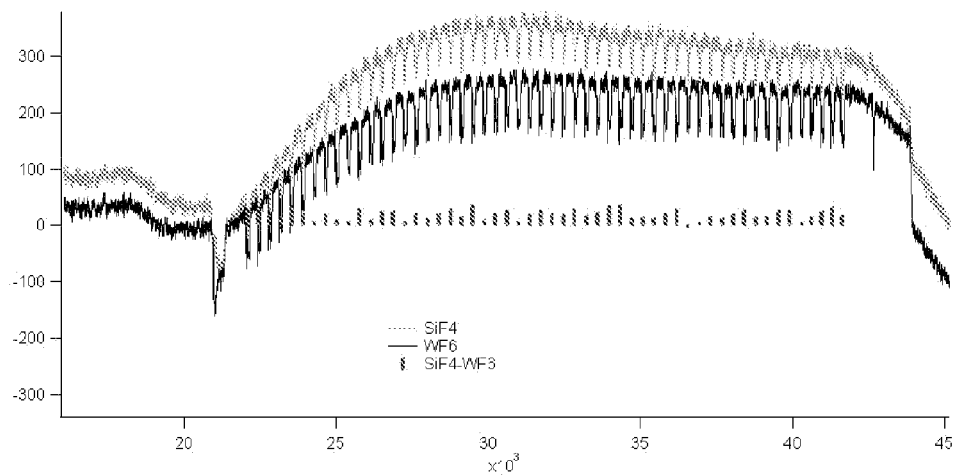
FIG. 33 is a graph of TPIR monitoring system output, showing peak height difference between silicon tetrafluoride and tungsten hexafluoride signals.

FIG. 33 shows a graph of peak height difference between $SiF_4$ and $WF_6$, together with the individual silicon tetrafluoride and tungsten hexafluoride output signals. The system for which data is shown in FIG. 33 does not have a GPN issue.

The foregoing algorithmic data analysis process has been illustratively described in respect of GPN monitoring of a tungsten hexafluoride CVD system. Such algorithmic process, however, is not limited to GPN monitoring applications, and the baseline and temperature correction procedures, as well as peak search and peak height (area) calculation, may be utilized in other TPIR monitoring applications. For example, the data analysis algorithmic process may be employed to calculate effluent concentrations, and temporal profiles can be used to calculate kinetic rates or other time sensitive information in chemical process monitoring or other applications.

The foregoing algorithmic data analysis process permits thermopile infrared detection systems to be calibrated and corrected for ambient radio frequency noise, short noise from electronics, and ambient temperature fluctuations.

In one embodiment, the data analysis process includes:
generating a TPIR monitoring output from a monitoring cell;
removing ambient radio frequency noise spikes to produce a first refined data output; smoothing the first refined data output using a binomial smoothing algorithm to produce a second refined data output;
calculating slope and offset values for signals of output components monitored in the gas cell;
utilizing the slopes and offsets for the monitored components to temperature correct the second refined output and produce a third refined output;
conducting a peak search algorithm of the third refined output and calculating peak heights of output components, to generate peak heights of such output components, and determining from peak height differences of such output components whether processing associated with the monitoring is within a predetermined operating regime; and
correspondingly modulating the process by adjustment of one or more operating parameters thereof.

For example, the predetermined operating regime in the case of tungsten CVD may be a regime free of GPN and/or Ti attack, arranged so that process conditions determined to be outside of such predetermined regime cause an output alarm to be generated, in addition to effecting control steps for the process to reestablish the desired operating regime.

Thus, the invention contemplates a process for controllably maintaining a process within a predetermined operating regime, using a TPIR monitoring and control system including a monitoring cell adapted to receive material from the process, wherein the material in the monitoring cell interacts with infrared radiation generated by the monitoring system and infrared radiation resulting from such interaction is detected by a TPIR detector of the TPIR monitoring and control system as a TPIR monitoring output from the monitoring cell, said process comprising:
generating a TPIR monitoring output from the monitoring cell;
removing ambient radio frequency noise spikes from TPIR monitoring output to produce a first refined data output;
smoothing the first refined data output using a binomial smoothing algorithm to produce a second refined data output;
calculating slope and offset values for signals of material components monitored in the monitoring cell;
utilizing the slopes and offsets for the monitored material components to temperature correct the second refined output and produce a third refined output;
conducting a peak search algorithm of the third refined output and calculating peak heights of the monitored material components, to generate peak heights of such monitored material components, and determining from peak height differences of such monitored material components whether processing associated with the monitoring is within a predetermined operating regime; and
correspondingly modulating the process by adjustment of one or more operating parameters thereof, to maintain the process within the predetermined operating regime.

In such process, the TPIR monitoring and control system can comprise a memory unit in which a data analysis algorithm and associated monitoring and control operational instructions for the process are stored, and from which the instructions are able to be accessed and executed by a monitoring and control system processor.

The process in one specific embodiment comprises a tungsten CVD process, and the predetermined operating regime comprises a process operating regime that is free of GPN and/or Ti attack.

The process can further comprise outputting an alarm when the process is determined to be outside the predetermined operating regime.

In another specific embodiment, the process comprises a chemical process producing an effluent, wherein the material from the process comprises effluent material, and the predetermined operating regime comprises effluent concentration below a predetermined value.

The invention in another aspect relates to a TPIR monitoring and control system, comprising:
a monitoring cell adapted to receive material for monitoring;
an infrared source arranged to emit radiation that interacts with material in the monitoring cell to produce output infrared radiation resulting from such interaction;
a TPIR detector arranged to detect the output infrared radiation and responsively generate a TPIR monitoring output for material monitored in the monitoring cell;
a computational module arranged for:
   generating a TPIR monitoring output from the monitoring cell;
   removing ambient radio frequency noise spikes from TPIR monitoring output to produce a first refined data output;
   smoothing the first refined data output using a binomial smoothing algorithm to produce a second refined data output;
   calculating slope and offset values for signals of material components monitored in the monitoring cell;
   utilizing the slopes and offsets for the monitored material components to temperature correct the second refined output and produce a third refined output;
   conducting a peak search algorithm of the third refined output and calculating peak heights of the monitored material components, to generate peak heights of such monitored material components, and determining from peak height differences of such monitored material components whether processing associated with the monitoring is within a predetermined operating regime; and
a controller coupled with the computational module for correspondingly modulating the process by adjustment of one or more operating parameters thereof, to maintain the process within a predetermined operating regime.

The TPIR monitoring and control system in a specific embodiment comprises a memory unit in which a data analysis algorithm and associated monitoring and control operational instructions are stored, and a processor arranged to access and execute such instructions.

Although the discussion herein has been primarily directed to tungsten CVD processes, many other CVD processes, e.g., for epi layer formation, polysilicon deposition, formation of SiN layers, and oxide formation, have associated process control and particle formation issues, in which monitoring in accordance with the present invention can be of value.

Other processes in which the monitoring apparatus and methodology of the invention can be beneficially employed include monitoring of the following specific deposition reactions:

$SiH_4+NH_3 \rightarrow SiN$

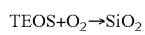
$TEOS+O_2 \rightarrow SiO_2$

$TDMAH(Hf)+TMA(Al)+O_3 \rightarrow HfO_2$ wherein TEOS is tetraethylorthosilicate, TDMAH(Hf) is tetrakis(dimethylamino)hafnium, and TMA(Al) is trimethylaluminum.

A further aspect of the invention relates to another infrared radiation monitoring technique for detecting occurrence of GPN in tungsten CVD systems.

Consistent with the earlier discussion herein, the chemistry of tungsten CVD involves two primary deposition reactions,

$SiH_4+WF_6 \rightarrow SiF_4+W+HF$ and

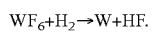
$WF_6+H_2 \rightarrow W+HF.$

The reaction of $SiH_4$ and $WF_6$ can occur in the gas phase if the $SiH_4$ concentration is much higher than the $WF_6$ concentration. Instead of deposition of tungsten on the surface of wafer, the gas phase reaction (gas phase nucleation, GPN) produces fine particles of tungsten (several nm to several hundred nm in size) that threaten the wafer quality. Therefore, the timing of introducing $SiH_4$ and $WF_6$ into the deposition chamber is critical for tungsten CVD to be efficiently conducted. In production facilities, wafers may be processed in batches of 50 or more.

The occurrence of GPN can result in such entire batches of wafers being rendered deficient or even useless for their intended purpose. When GPN occurs, a "cloud" of fine particles is typically created in the deposition tool chamber.

The invention contemplates monitoring the deposition chamber with an infrared radiation diode laser arranged at a window of the chamber to transmit IR radiation into the gas volume in the interior of the chamber during tungsten CVD operation. The laser beam radiation when encountering a GPN "cloud" is scattered, and the resulting burst of backscatter IR radiation can be detected by an appropriately positioned photodiode detector.

Alternatively, the CVD chamber may be arranged with oppositely facing windows, one being arranged for incident transmission of IR radiation therethrough from the laser diode, and the other window being arranged for transmission of exiting radiation to an in-line or otherwise appropriately positioned photodiode detector (e.g., when a mirror/lens arrangement is employed to conduct exiting radiation to the detector). In such transmissivity detection arrangement, the occurrence of GPN will act to attenuate the incident radiation beam and the detected signal will therefore be correlative of such occurrence of GPN.

The above-discussed IR laser and photodiode detector arrangement can be integrated with an existing control system of a tungsten CVD installation, and may be constructed to stop the deposition operation to facilitate establishment of non-GPN conditions. Alternatively, the IR source and detector apparatus may be adapted to provide an output signal indicative of the presence or absence of GPN conditions, with such output signal being utilized to control the CVD process equipment so that non-GPN conditions are established without cessation of CVD operation.

The use of an infrared radiation laser source in the above-discussed monitoring systems will avoid ambient light interference with the IR radiation, and is readily retrofitted to an existing CVD installation.

The features and advantages of the invention are more fully shown by the following non-limiting example.

Example 1

Real-time detection of gas phase nucleation by monitoring the tungsten chemical vapor deposition (WCVD) reaction gases was conducted, using an NDIR (non-dispersive infrared) spectrometer with a built-in analog/digital (A/D) data acquisition system installed in the foreline of a commercial WCVD tool. The device was installed within a process gas flow segment of the reactor where a clear and direct optical path existed between the IR light source and the detector unit.

A TPIR system of the type shown in FIG. 3 was used, comprising a) a broadband IR source, b) a variable pathlength sampling region and c) a 4-channel thermopile detector unit. The system was capable of monitoring and recording four (4) separate and discrete gas species, simultaneously. A narrow band-pass filter was selected for each thermopile channel that directly correlated to the IR absorption band for a specific gaseous species. When multiple absorption wavelengths existed for a specific gas, a wavelength was selected that did not overlap with the absorption of the other gases present in the system, in order to minimize interferences observed from the specific gases.

The thermopile detector measured the temporal temperature change on the sensor element and was directly correlated to the incident IR intensity resulting from the absorption of that specific gas. The spectrometer was calibrated with pre-mixed gases of known concentrations.

Figure 34:
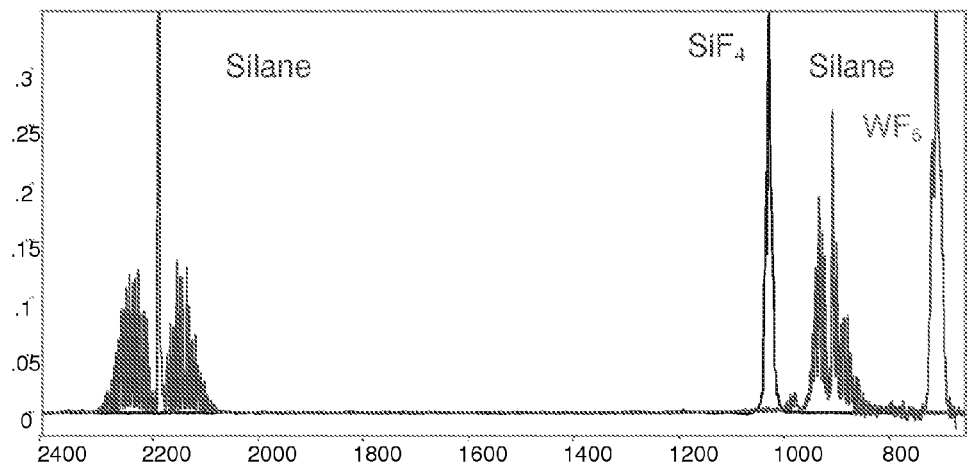
FIG. 34 shows spectra collected for WCVD process gases and by-products involved in the WCVD nucleation stage, including IR absorption bands for $SiH_4$, $WF_6$ and $SiF_4$.

FIG. 34 shows spectra collected for WCVD process gases and by-products involved in the WCVD nucleation stage, including IR absorption bands for $SiH_4$, $WF_6$ and $SiF_4$. The corresponding IR bandpass filters were specifically selected to match the v3 (W—F stretch at 712 cm-1), v3 (Si—H stretch at 2191 cm-1) and v3 (Si—F stretch at 1032 cm-1) bands for $WF_6$, $SiH_4$ and $SiF_4$, respectively. The v3 band of $SiF_4$ overlaps with (v1+v2) combination band of $SiH_4$ at ~1060 cm-1. Since the $SiH_4$ reactant was largely consumed during the nucleation step of the WCVD reaction and the combination band intensity is usually orders of magnitude weaker at room temperature, the contribution from (v1+v2) band of $SiH_4$ to the v3 band of $SiF_4$ was negligible. The fourth detector channel was blanked off and used as a reference channel.

Figure 35:
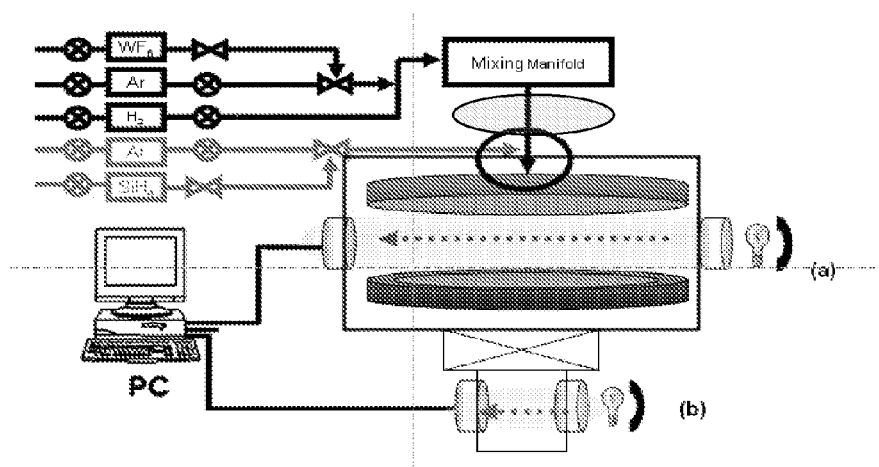
FIG. 35 is a schematic representation of the deposition system, the TPIR system and the data acquisition system, in an illustrative arrangement for carrying out TPIR monitoring.

FIG. 35 is a schematic representation of the deposition system, the TPIR system and the data acquisition system. This arrangement provides three potential, but distinct set-ups for use in collecting the TPIR analytical data: (a) TPIR monitoring across the actual wafer processing chamber and (b) TPIR monitoring across the fore-line pumping region, downstream from the actual wafer processing region and (c) TPIR monitoring at the outlet of the gas mixing manifold region prior to the wafer processing chamber, near the actual gas entry zone. Due to space and optical path considerations, the TPIR system was implemented within region (b), downstream from the wafer processing chamber and in the exhaust foreline segment.

The IR source and the detector units were mounted on each side of a spool piece on the foreline, with the spool flange used as the gas sampling region. The IR light entered and exited the spool flange through a pair of ZnSe windows. A voltage signal from the thermopile detector was digitized with a built-in A/D converter and sent to a laptop computer (PC) for data collection and analysis using software developed by ATMI, Inc., Danbury, Conn., USA. A feedback-control-loop-system was arranged to send an automated command to the process tool, both to control the process and to automatically stop the tool when gas phase nucleation (GPN) was detected.

Two sets of experiments were performed to correlate visual GPN observations with infrared analysis. The first set of tests was carried out using a single pass configuration for the TPIR spectrometer with a sampling pathlength of 0.33 meters. The second set of tests used a multi-pass configuration with a total sampling pathlength of 2.0 meters. The factors that were identified as causing GPN included substrate temperature, total pressure, and $SiH_4/WF_6$ ratio. Wafer temperature was precisely controlled and monitored by the manufacturing tool.

The major cause of GPN relates to poorly functioning gas delivery systems, including clogging of gas filters, clogging of mass-flow controllers, changing response times of mass flow controllers and pneumatic valve failures or delays. Each of these malfunctions can cause a change of delivery timing of $SiH_4$ and $WF_6$ and/or their respective partial pressures and concentrations. To confirm this, different valve delays and $SiH_4/WF_6$ flow rates were tested experimentally to demonstrate a correlation to GPN.

The TPIR system was used to measure the gas-phase concentrations of $SiF_4$, $WF_6$, and $SiH_4$ at a 4 Hz sampling rate. The change in observed peak intensity, between $WF_6$ and $SiF_4$, directly correlates to GPN and was used to determine the onset of GPN. The TPIR data were also compared to a visible inspection method used to control the WCVD process.

Single-Pass Gas Analysis

Designed experiments were conducted to examine the effect of specific variables on the onset of GPN and to examine related TPIR responses using a single pass gas cell configuration. The first set of designed experiments consisted of a 3 factor-full-factorial-design and replication tests, as shown in Table 1 below. Also shown in Table 1 are the TPIR responses and complimentary results from visual inspection of the process. TPIR responses showed excellent agreement with the visual inspection results.

TABLE 1

| RUN | VALVE DELAY | $SiH_4$ FLOW | $WF_6$ FLOW | TPIR detection | VISUAL RESULT |
| --- | --- | --- | --- | --- | --- |
| 1 | 1.4 | 40 | 300 | 0 | No GPN Observed |
| 2 | 1.8 | 40 | 300 | 300 | Heavy GPN Observed |
| 3 | 1 | 40 | 300 | 0 | No GPN Observed |
| 4 | 1.4 | 50 | 300 | 0 | No GPN Observed |
| 5 | 1.4 | 30 | 300 | 0 | No GPN Observed |
| 6 | 1.4 | 40 | 250 | 200 | Medium GPN Observed |
| 7 | 1.4 | 40 | 350 | 0 | No GPN Observed |
| 8 | 1.5 | 40 | 300 | 0 | No GPN Observed |
| 9 | 1.6 | 40 | 300 | 320 | Heavy GPN Observed |
| 10 | 1.7 | 40 | 300 | 200 | Medium GPN Observed |
| 11 | 1.4 | 30 | 350 | 0 | No GPN Observed |
| 12 | 1.4 | 50 | 250 | 300 | Heavy GPN Observed |

Since the TPIR spectrometer was installed on the exhaust foreline region of the process tool, it was possible to monitor the reaction effluents, after gases underwent chemical reaction within the CVD process chamber, including both unreacted gases and reaction by-products. The expected IR active gases within the reaction effluent were $WF_6$ and $SiF_4$. Little or no $SiH_4$ was observed, since most of the $SiH_4$ was consumed in the CVD reaction, being readily converted to $SiF_4$, and displaying a relatively small IR cross-section. Given that $SiF_4$ was a major reaction by-product of the $SiH_4$ reduction, the [$SiH_4$] concentration was extrapolated from the [$SiF_4$] signal. The $SiF_4/WF_6$ ratio is proportional to the $SiH_4/WF_6$ ratio, thereby allowing an indirect measure of the reaction ratio that induces GPN. The concentration of $SiF_4/SiHF_3$ during WCVD reactions varied depending on the flow ratios of reactants and the extent of GPN. The $SiF_4$ infrared data included both $SiF_4$ and $SiHF_3$ since they share similar IR absorbance regions.

Figure 36:
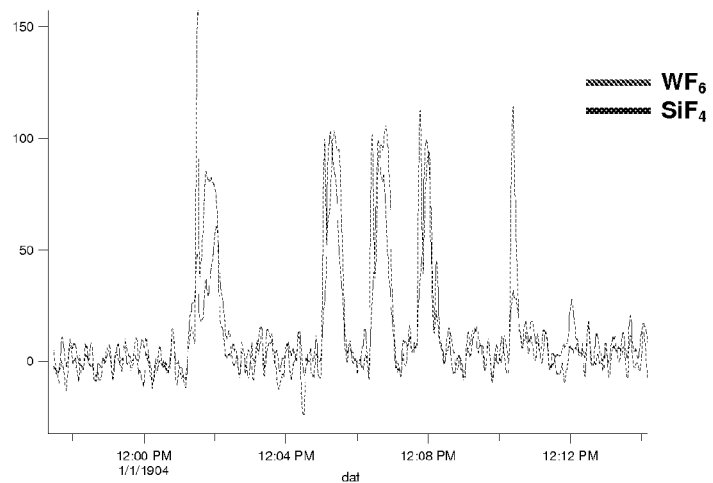
FIG. 36 is a graph of spectral data collected with the TPIR system during monitoring of the WCVD process without occurrence of gas phase nucleation.

FIG. 7, previously described, and FIG. 36 are graphs of spectral data collected with the TPIR system during monitoring of the WCVD process. Five spectral peaks are shown, separated temporally (from left to right) and associated with the WCVD manufacturing process. The first peak is associated with a pre-coating process, while the following three (3) peaks result from the actual WCVD process. The last peak on the right of each figure (intense red peak) was associated with the tool venting step after completion of the WCVD process. During the actual WCVD process steps, the intensity of the $SiF_4$ peak (blue line) was higher than the intensity of the red line ($WF_6$), as shown in FIG. 36. These spectral characteristics were noted when gas-phase nucleation occurred, as confirmed by visual inspection.

As shown in FIG. 36, when the spectral intensities of $WF_6$ and $SiF_4$ were similar, no gas-phase nucleation was observed.

The ratio of $WF_6$ to $SiF_4$ provided a strong correlation to GPN during the WCVD process, as confirmed by visual inspection of both scenarios.

The results of the designed experiments were analyzed both quantitatively and qualitatively. Based upon the collection of numerous spectra and comparison to visual inspection of the WCVD process, a mathematical algorithm was developed to account for the probability that GPN would occur during the WCVD process. By examining the intensities and relative ratio of $[WF_6]$ to $[SiF_4]$ concentrations, it was calculated when GPN would occur.

FIG. 8, previously described, shows IR spectral data obtained during the WCVD process with the TPIR system, with the relative position of the processed spectral data and gas concentration ratio providing a direct correlation to the absence or presence of GPN. A line that delineates the presence or absence of GPN during the WCVD process, is shown in FIG. 8, and equals the arbitrary value of −15. Above this value, no GPN was observed, while below this value corresponds to GPN. Further, the greater the difference between −15 and the actual calculated run value, the more intense was the formation of GPN.

The invention therefore contemplates a predictive model for determining when GPN will occur in the WCVD process. Alternatively, direct integration of the TPIR monitoring capability with the deposition tool enables arrangements to be implemented in which the reactor settings are altered, or WCVD process is stopped, to avoid the occurrence of GPN. In either scenario, the performance of the process tool can be optimized, thereby reducing waste and increasing yield of product devices manufacturable by the CVD system.

These observations provided the basis for the following general equations for the absence or presence of GPN, based on the single-pass, in-situ spectroscopic analysis of the WCVD process:

If ($[WF_6]-[SiF_4]$) relative difference was >−15: No GPN was observed

If ($[WF_6]-[SiF_4]$) relative difference was <−15: GPN was observed

Figure 37:
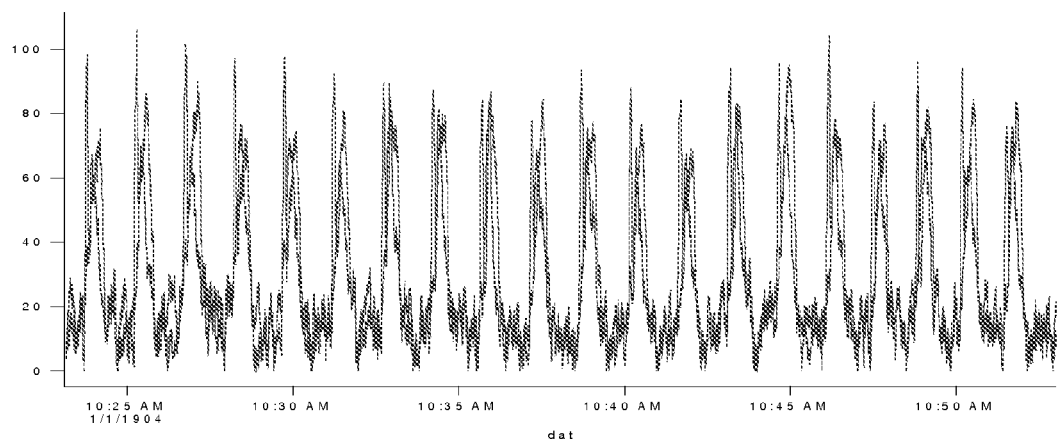
FIG. 37 shows IR spectral data obtained during the WCVD process with the TPIR system, indicating the absence of GPN.

FIG. 37 shows the spectral data obtained by continuous monitoring of product wafers by a single-pass TPIR system installed on a WCVD tool for an extended period of continuous wafer processing time. The variability in spectral intensity during the manufacturing process was noted by comparing the relative intensities of $WF_6$ (red) to $SiF_4$ (blue). Even though the spectral intensity levels fluctuated throughout these runs, the relative ratios indicated no strong presence of GPN during the entire wafer processing sequence. Throughout a marathon run of over 12,000 wafers, the feasibility of using the TPIR diagnostic technology for the in-situ monitoring of the WCVD process, was demonstrated.

Multi-pass Gas Analysis

To further improve the signal-to-noise ratio (S/N) of the spectral data obtained during the process, a multi-pass optical system was designed, implemented and tested within the same configuration as the single-pass system. Similar designed experiments were then performed specifically to monitor the WCVD process and test the previously developed GPN methodology. The results of the designed experiments, using the multi-pass optical configuration, are summarized in Table 2 below, for the set of 3 full factorial designed experiments, along with results of the visual inspection method.

TABLE 2

| RUN | VALVE DELAY | $SiH_4$ FLOW | $WF_6$ FLOW | IR detection | VISUAL RESULT |
|---|---|---|---|---|---|
| 1 | 0.8 | 40 | 300 | 0 | No GPN Observed |
| 2 | 1.0 | 40 | 300 | 320 | Heavy GPN Observed |
| 3 | 0.7 | 50 | 300 | 320 | Heavy GPN Observed |
| 4 | 0.7 | 30 | 300 | 0 | No GPN Observed |
| 5 | 0.7 | 40 | 250 | 0 | No GPN Observed |
| 6 | 0.8 | 40 | 350 | 0 | No GPN Observed |
| 7 | 0.6 | 50 | 300 | 200 | Medium GPN Observed |
| 8 | 1.0 | 50 | 300 | 320 | Heavy GPN Observed |
| 9 | 1.0 | 30 | 300 | 0 | No GPN Observed |

Figure 38:
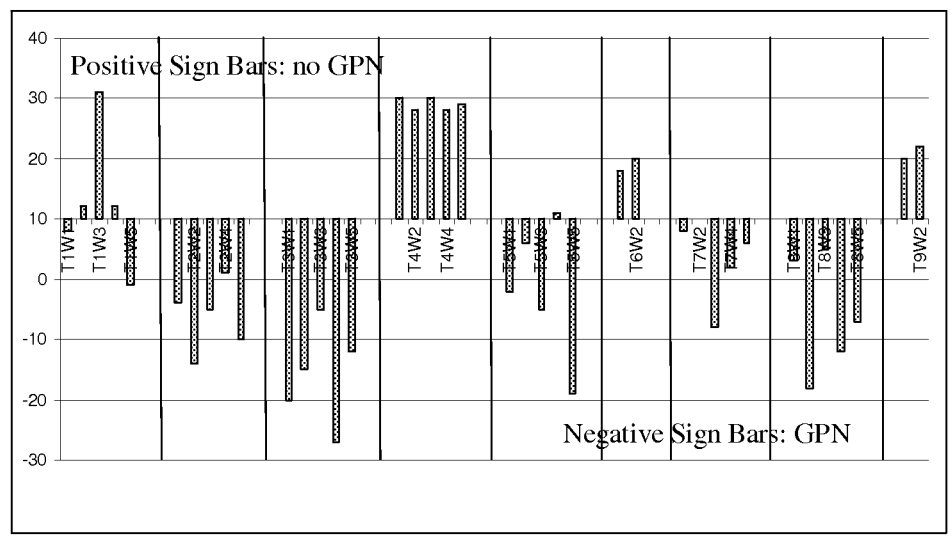
FIG. 38 shows the IR spectral data that were obtained during the WCVD process using the multi-pass TPIR system and that were processed to indicate conditions that specifically result in GPN, based upon the analysis of measured $WF_6$ and $SiF_4$ signal intensities and ratios.

FIG. 38 shows the IR spectral data that were obtained during the WCVD process using the multi-pass TPIR system and that were processed to indicate conditions that specifically result in GPN, based upon the analysis of measured $WF_6$ and $SiF_4$ signal intensities and ratios. It is noted that the relative position designating the onset of GPN has changed with the multi-pass optical design when compared to the single-pass system.

When reviewing all of the designed experimental data, in light of the measured in-situ spectral data, it is clear that two WCVD factors are critical and therefore, must be accurately controlled. To avoid random GPN during WCVD, the valve delay time (time delay prior to the introduction of $WF_6$ into the deposition chamber) and the $SiH_4$ flow rate were both observed to be critical. Each of these factors can cause a high ratio of $SiH_4/WF_6$ within an extremely short time period. Less than 0.3 sec change in the valve delay time, or less than 20 sccm in $SiH_4$ flow rate variation, was enough to completely change the WCVD process, transitioning from the absence of GPN to the onset of GPN. It was not surprising that the flow rate of $WF_6$ appeared to have the most negligible effect on GPN, since $WF_6$ was usually in excess when compared with $SiH_4$ and was introduced later. In most cases, the $SiH_4$ introduced was quantitatively consumed and directly converted to $SiF_4$. Excess $WF_6$ during the WCVD process may negatively affect the contact resistance of the TiN barrier film.

Concerning the operative GPN mechanism, the spectral observations were consistent with GPN proceeding through an initial decomposition of $SiH_4$ to form Si (y>=2) centers or small clusters. The silicon clusters, once formed, can act as nuclei for particle growth through subsequent reactions, as noted below:

$2SiH_4 \rightarrow Si(s)$ $x\,WF_6 + Si(y) \rightarrow W_xSi_y + SiF_4$ $W_xSi_y + zSiH_4 \rightarrow W_xSi_{(y+z)} + H_2$ The short delay time allows $SiH_4$ to form silicon clusters and bypass the surface nucleation step. The higher ratio of $SiH_4/WF_6$ also causes excess $SiH_4$ to form silicon clusters.

In summary, WCVD has two significant process failure modes, gas-phase nucleation and Ti barrier attack. Titanium barrier attack is affected by excessive $WF_6$ reactant, whereas GPN is more clearly related to excessive $SiH_4$ reactant and the relative ratio of $WF_6$ to $SiH_4$.

In-situ process monitoring utilizing thermopyroelectric infrared (TPIR) spectroscopy enables effective control of the WCVD process to be achieved. Real-time GPN monitoring, using TPIR spectrometry, provided excellent correlation between the WCVD effluent concentrations, their relative ratios and GPN, as confirmed by visual observations. The spectrometer is capable of detecting and predicting GPN, and is a useful diagnostic in manufacturing operations, as well as being capable of minimizing the titanium barrier attack by measuring the $WF_6$ reactant gas during the process.

The TPIR system and method of the invention deliver reliable, real-time detection of GPN that is superior to visual inspection methods. The TPIR system and method of the invention are highly flexible, providing real-time feedback for both gas-blending and process monitoring. Both single-pass and multi-pass systems can be utilized effectively for optimization of the WCVD process. The spectroscopic technique of the invention can be extended to other processes where chemical control and reaction sequencing are critical. It will be understood that in application to WCVD applications, the TPIR system can be readily integrated with the WCVD manufacturing process tool, to achieve effective real time communication and process control.

What is claimed is:

1. An apparatus for monitoring and control of a vapor deposition installation wherein a gas mixture containing gas species can cause gas phase nucleation and/or chemical attack under process conditions supportive of such behavior, the monitoring and control apparatus comprising:
   a radiation source arranged to transmit source radiation through a sample of said gas mixture;
   a detector arranged to receive output radiation resulting from interaction of the source radiation with the gas mixture sample, and to responsively generate a detector output; and
   a processor and control assembly, comprising an algorithmic program for determining incipient occurrence of gas phase nucleation and/or chemical attack, the processor being configured to receive the detector output, algorithmically process same according to the algorithmic program to determine incipient occurrence of said gas phase nucleation and/or chemical attack in the vapor deposition installation, and responsively generate an output to control the vapor deposition installation so as to avoid gas phase nucleation and/or chemical attack therein, and maintain the vapor deposition installation in non-gas phase nucleation and/or non-chemical attack operation throughout vapor deposition in the vapor deposition installation.

2. The apparatus of claim 1, wherein the processor is adapted to determine incipient occurrence of said gas phase nucleation and/or chemical attack in the vapor deposition installation, by operation according to the algorithmic program including at least one of the following:
   (i) determination of peak heights of one or more gas species of the gas mixture;
   (ii) determination of differences in peak heights between two or more of the gas species of the gas mixture;
   (iii) determination of ratios of peak heights of two or more of the gas species of the gas mixture;
   (iv) determination of AUC of a spectral portion of the output radiation for one or more gas species of the gas mixture;
   (v) determination of differences of AUC for spectral portions of the output radiation for two or more gas species of the gas mixture;
   (vi) determination of ratios of AUC for spectral portions of the output radiation for two or more gas species of the gas mixture;
   (vii) determination of slope of a spectral curve in a spectral portion of the output radiation of one or more gas species of the gas mixture;
   (viii) determination of differences of slopes of spectral curves in spectral portions of the output radiation of two or more gas species of the gas mixture;
   (ix) determination of ratios of slopes of spectral curves in spectral portions of the output radiation of two or more gas species of the gas mixture;
   (x) determination of peak heights of the output radiation of one or more gas species of the gas mixture at a predetermined point in time;
   (xi) determination of differences in peak heights of the output radiation between two or more of the gas species of the gas mixture at a predetermined point in time;
   (xii) determination of ratios of peak heights of the output radiation of two or more of the gas species of the gas mixture at a predetermined point in time; and
   (xiii) monitoring of a gas species reactant that is consumed during vapor deposition, as an indicator of onset of gas phase nucleation and/or chemical attack.

3. The apparatus of claim 1, wherein the processor and control assembly includes a database of spectra or spectral characteristics of gas species of interest in the gas mixture, and the processor is arranged to process the detector output against the database to determine incipient occurrence of said gas phase nucleation and/or chemical attack throughout the vapor deposition in the vapor deposition installation.

4. The apparatus of claim 1, as operatively coupled with a chemical vapor deposition system arranged for deposition of tungsten from a source gas mixture including silane and tungsten hexafluoride.

5. The apparatus of claim 4, wherein the chemical vapor deposition system comprises a chemical vapor deposition chamber having one or more windows, wherein the radiation source comprises an infrared radiation diode laser arranged to transmit IR radiation through a window into the chamber for interaction with vapor of the gas mixture therein during chemical vapor deposition in the chamber to generate the output radiation from such interaction, and the detector comprises a photodiode detector arranged to receive said output radiation transmitted through a same or different window of the chamber and to responsively generate the detector output.

6. The apparatus of claim 5, wherein the chemical vapor deposition chamber is arranged in an arrangement in which:
   (A) the chemical vapor deposition chamber comprises a single window, and the photodiode detector is arranged for detecting back-scatter IR radiation; or
   (B) the chemical vapor deposition chamber comprises two windows in opposing registration with one another, with the infrared radiation diode laser being arranged for transmitting IR radiation through a first one of said windows, and the photodiode detector being arranged for detecting output radiation transmitted through a second one of said windows.

7. The apparatus of claim 1, as adapted for monitoring of at least one of $WF_6$, $SiF_4$ and $SiH_4$, wherein the radiation source is arranged to transmit infrared radiation, and the detector comprises a TPIR detector.

8. The apparatus of claim 1, comprising:
   a monitoring cell adapted to receive the sample of said gas mixture for monitoring;
   and wherein:
   the radiation source comprises an infrared source that transmits infrared radiation through the sample of said gas mixture in the monitoring cell;
   the detector comprises a TPIR detector; and
   the algorithmic program of the processor and control assembly is configured so that the processor in determining incipient occurrence of said gas phase nucleation and/or chemical attack in the vapor deposition installation, performs an algorithmic process comprising removing ambient radio frequency noise spikes from the TPIR detector output to produce a first refined data output;

smoothing the first refined data output using a binomial smoothing algorithm to produce a second refined data output;

calculating slope and offset values for signals of gas mixture components monitored in the monitoring cell;

utilizing the slopes and offsets for the monitored gas mixture components to temperature correct the second refined output and produce a third refined output;

conducting a peak search algorithm of the third refined output and calculating peak heights of the monitored gas mixture components, to generate peak heights of such monitored gas mixture components, and determining from peak height differences of such monitored gas mixture components whether incipient occurrence of said gas phase nucleation and/or chemical attack in the vapor deposition installation is identified, as predictive of actual occurrence of said gas phase nucleation and/or chemical attack in the vapor deposition installation in the absence of modulation of the vapor deposition installation; and the processor and control assembly comprises a controller coupled with the processor for correspondingly modulating the vapor deposition installation to avoid gas phase nucleation and/or chemical attack therein, and maintain the vapor deposition installation in non-gas phase nucleation and/or non-chemical attack operation throughout the vapor deposition in the vapor deposition installation.

9. The apparatus of claim 8, wherein the processor and control assembly comprises a memory unit in which the algorithmic program and associated monitoring and control operational instructions are stored, and the processor is arranged to access and execute said instructions.

\* \* \* \* \*

UNITED STATES PATENT AND TRADEMARK OFFICE
CERTIFICATE OF CORRECTION

PATENT NO. : 9,340,878 B2  
APPLICATION NO. : 13/375053  
DATED : May 17, 2016  
INVENTOR(S) : Jose I. Arno et al.

Page 1 of 1

It is certified that error appears in the above-identified patent and that said Letters Patent is hereby corrected as shown below:

In the Specification

Column 11, line 66: "(AH)" should be --$\Delta H$--.

Signed and Sealed this  
Ninth Day of August, 2016

Michelle K. Lee  
*Director of the United States Patent and Trademark Office*